(12) United States Patent
Chin et al.

(10) Patent No.: US 8,257,355 B2
(45) Date of Patent: Sep. 4, 2012

(54) METHODS AND DEVICES FOR STATIC OR DYNAMIC SPINE STABILIZATION

(75) Inventors: Kingsley Richard Chin, Philadelphia, PA (US); Christopher A. Chang, Beverly, MA (US)

(73) Assignee: Spinefrontier Inc., Beverly, MA (US)

( * ) Notice: Subject to any disclaimer, the term of this patent is extended or adjusted under 35 U.S.C. 154(b) by 933 days.

(21) Appl. No.: 11/758,809

(22) Filed: Jun. 6, 2007

(65) Prior Publication Data
US 2007/0299448 A1 Dec. 27, 2007

Related U.S. Application Data

(60) Provisional application No. 60/811,593, filed on Jun. 7, 2006.

(51) Int. Cl.
*A61B 17/56* (2006.01)
*A61B 17/58* (2006.01)
*A61B 17/80* (2006.01)
*A61B 17/88* (2006.01)
*A61B 17/04* (2006.01)
*A61B 17/86* (2006.01)
*A61F 2/30* (2006.01)
*A61F 2/08* (2006.01)

(52) U.S. Cl. .......... 606/70; 606/281; 606/284; 606/286; 606/304

(58) Field of Classification Search .................... 606/71, 606/281, 283, 284, 286, 304
See application file for complete search history.

(56) References Cited

U.S. PATENT DOCUMENTS

| | | | |
|---|---|---|---|
| 5,545,163 A * | 8/1996 | Miller et al. | 606/287 |
| 6,340,362 B1 * | 1/2002 | Pierer et al. | 606/71 |
| 7,090,676 B2 * | 8/2006 | Huebner et al. | 606/71 |
| 7,559,929 B2 * | 7/2009 | Denti | 606/86 A |
| 2002/0169453 A1 | 11/2002 | Berger | |
| 2003/0114856 A1 * | 6/2003 | Nathanson et al. | 606/70 |
| 2003/0144666 A1 | 7/2003 | Bagga et al. | |
| 2003/0153913 A1 | 8/2003 | Altarac et al. | |
| 2003/0187443 A1 | 10/2003 | Lauryssen et al. | |
| 2004/0006343 A1 * | 1/2004 | Sevrain | 606/61 |
| 2004/0034352 A1 | 2/2004 | Needham et al. | |
| 2004/0039387 A1 | 2/2004 | Gause et al. | |
| 2004/0177847 A1 | 9/2004 | Foley et al. | |
| 2004/0243128 A1 * | 12/2004 | Howland | 606/61 |
| 2005/0027298 A1 | 2/2005 | Michelson | |
| 2005/0038434 A1 | 2/2005 | Mathews | |
| 2005/0143823 A1 | 6/2005 | Boyd et al. | |
| 2005/0182404 A1 | 8/2005 | Lauryssen et al. | |
| 2006/0122605 A1 | 6/2006 | Suh et al. | |
| 2006/0122607 A1 | 6/2006 | Kolb | |
| 2006/0195089 A1 | 8/2006 | LeHuec et al. | |
| 2006/0235385 A1 | 10/2006 | Whipple | |

(Continued)

*Primary Examiner* — Kevin T Truong
*Assistant Examiner* — David Bates
(74) *Attorney, Agent, or Firm* — AKC Patents LLC; Aliki K. Collins

(57) ABSTRACT

Methods and devices for static or dynamic spine stabilization include an anterior plating system that allows longitudinal and pivoting motion of the plates and of the stabilized vertebras. In one embodiment a spine fixation assembly for connecting a first vertebra to a second vertebra includes a first plate configured to be attached to one or more locations of the first vertebra and a second plate configured to be attached to one or more locations of the second vertebra. The first plate is pivotally connected to the second plate and may also allow longitudinal and/or horizontal motion of the plates relative to each other.

13 Claims, 24 Drawing Sheets

U.S. PATENT DOCUMENTS

| | | | |
|---|---|---|---|
| 2006/0264962 A1* | 11/2006 | Chin et al. | 606/90 |
| 2006/0276793 A1 | 12/2006 | Berry | |
| 2006/0276794 A1* | 12/2006 | Stern | 606/69 |
| 2006/0293684 A1 | 12/2006 | Shluzas et al. | |
| 2007/0093831 A1 | 4/2007 | Abdelgany et al. | |
| 2007/0233094 A1* | 10/2007 | Colleran et al. | 606/61 |

* cited by examiner

METHODS AND DEVICES FOR STATIC OR DYNAMIC SPINE STABILIZATION

CROSS REFERENCE TO RELATED CO-PENDING APPLICATIONS

This application claims the benefit of U.S. provisional application Ser. No. 60/811,593 filed Jun. 7, 2006 and entitled "METHODS AND DEVICES FOR STATIC OR DYNAMIC SPINE STABILIZATION", the contents of which are expressly incorporated herein by reference.

FIELD OF THE INVENTION

The present invention relates to methods and devices for static or dynamic spine stabilization, and more particularly to methods and devices including an anterior plating system that allows longitudinal and pivoting motion of the plates and therefore of the stabilized vertebras.

BACKGROUND OF THE INVENTION

The human spine consists of individual vertebras (segments) that are connected to each other. Under normal circumstances the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal, achieve stability, protect the neural structures, or to relief the patient of discomfort. The goal of spine surgery for a multitude of spinal disorders especially those causing compression of the neural structures is often decompression of the neural elements and or fusion of adjacent vertebral segments. Fusion works well because it stops pain due to movement at the facet joints or intervertebral discs, holds the spine in place after correcting deformity, and prevents instability and or deformity of the spine after spine procedures such as laminectomies or corpectomies.

Anterior decompression directly removes anterior compressive structures and is known to have improved results in these cases over indirect decompression afforded by laminectomies. Anterior discectomy and fusion or anterior corpectomy and fusion are most commonly performed in the cervical spine but there is increasing application in the thoracic and lumbar spine.

In recent years, there is an increase in the use of plate fixation to stabilize the cervical spine after anterior decompression and fusion. (U.S. Pat. No. 6,402,756, U.S. Pat. No. 5,616,142, U.S. Pat. No. 5,800,433 and U.S. Publication No. 2002-0111630, U.S. Pat. No. 6,328,738) The goals of plate fixation include increased stability to allow for less reliance on rigid external orthosis such as hard cervical collars and halos for stability. It is thought that plates also increased the rate of fusion and decreased the incidence of graft complications such as graft extrusions and subsidence. One of the disadvantages of current anterior cervical plates includes the lack of graft subsidence and continuous graft loading which is believed to be advantageous for fusion. It is also difficult to place the plate in a straight line longitudinally between adjacent vertebras and plates are therefore often inadvertently placed at an angle. These technical difficulties often lead to a higher rate of complications including failure of the graft to fuse (pseudoarthrosis) and failure of the moveable (dynamic) mechanism to work, or failure of the plate-screw interface due to abnormal angular and rotational forces.

The newest plating systems have been designed to allow motion between the segments to be fused either at the fixation points between the plate and the screws or as a sliding mechanism within the plate with the ends of the plate fixed to screws in the vertebral body. This new "dynamic" plating system is believed to offer superior fusion rates since it allows continuous graft loading and natural graft subsidence while acting as a block to anterior graft displacement.

However, the limitations of dynamic plating systems include, potential failure of the moveable mechanism to work if the plates are placed at an angle between the vertebral bodies to be fused, lack of bidirectional movements during compression (neck flexion) and distraction (extension and lying supine), and lack of variable compression rates during sudden neck movements. Accordingly there is a need for an improved dynamic stabilization system that addresses the above-mentioned limitations.

SUMMARY OF THE INVENTION

Methods and devices for static or dynamic spine stabilization include an anterior plating system that allows longitudinal and pivoting motion of the plates and of the stabilized vertebras.

In general, in one aspect, the invention features a spine fixation assembly for connecting a first vertebra to a second vertebra including one or more guide wires, one or more fixation elements, a plate and one or more locking elements. One or more guide wires are configured to be inserted into one or more locations of the first vertebra and one or more guide wires are configured to be inserted into one or more locations of the second vertebra. One or more fixation elements are configured to be driven into the one or more locations of the first vertebra and one or more fixation elements are configured to be driven into the one or more locations of the second vertebra, respectively. Each of the fixation elements comprises a threaded body, a flange extending from an end of the threaded body, a threaded post extending from the flange and a through bore extending longitudinally through the threaded body the flange and the post, and the corresponding guide wire is dimensioned to pass through the through bore. The plate is configured to be placed over the threaded posts of the one or more fixation elements driven into the one or more locations of the first vertebra and over the threaded posts of the one or more fixation elements driven into the one or more locations of the second vertebra, and to overlay the vertebras. The plate comprises one or more apertures configured to receive the one or more fixation elements. One or more locking elements are configured to attach each of the posts of the one or more fixation elements to the plate, thereby securing the plate to the one or more fixation elements.

Implementations of this aspect of the invention may include one or more of the following features. The plate comprises an hourglass shape and an hourglass central aperture and the hourglass aperture is configured to provide access and line of vision to the under laying first and second vertebras and to an intervertebral space between the first and second vertebras. The apertures are dimensioned to allow the posts to pass through and the flanges not to pass through, so that the plate sits on top of the flanges. The locking elements comprise threads dimensioned to engage threads in the posts. The first vertebra may be adjacent or not adjacent to the second vertebra. The first and second vertebras may be separated by at least a third vertebra and the plate is dimensioned to overlie the first, second and third vertebras. The spine assembly may further include one or more additional fixation elements configured to be driven into one or more locations of the third vertebra and wherein the plate comprises one or more additional apertures configured to receive the one or more additional fixation elements.

In general in another aspect the invention features a spine fixation method for connecting a first vertebra to a second vertebra including the following steps. First, inserting one or more guide wires into one or more locations of the first vertebra and one or more guide wires into one or more locations of the second vertebra. Next, driving one or more fixation elements into the one or more locations of the first vertebra and one or more fixation elements into the one or more locations of the second vertebra, respectively. Each of the fixation elements comprises a threaded body, a flange extending from an end of the threaded body, a threaded post extending from the flange and a through bore extending longitudinally through the threaded body the flange and the post, and the corresponding guide wire passes through the through bore. Next, placing a plate over the threaded posts of the one or more fixation elements driven into the one or more locations of the first vertebra and over the threaded posts of the one or more fixation elements driven into the one or more locations of the second vertebra. The plate is configured to overlay the vertebras and comprises one or more apertures configured to receive the one or more fixation elements. Finally, attaching a locking element to each of the posts of the one or more fixation elements thereby securing the plate to the one or more fixation elements.

In general in another aspect the invention features a spine fixation assembly for connecting a first vertebra to a second vertebra including a first plate configured to be attached to one or more locations of the first vertebra, a second plate configured to be attached to one or more locations of the second vertebra. The first plate is pivotally connected to the second plate.

Implementations of this aspect of the invention may include one or more of the following features. The spine fixation assembly may further include one or more guide wires configured to be inserted into the one or more locations of the first vertebra and one or more guide wires configured to be inserted into the one or more locations of the second vertebra. One or more fixation elements are configured to be driven into the one or more locations of the first vertebra and one or more fixation elements are configured to be driven into the one or more locations of the second vertebra, respectively. Each of the fixation elements comprises a threaded body, a flange extending from an end of the threaded body, a threaded post extending from the flange and a through bore extending longitudinally through the threaded body the flange and the post, and the corresponding guide wire is dimensioned to pass through the through bore. The first plate is configured to be placed over the threaded posts of the one or more fixation elements driven into the one or more locations of the first vertebra and the second plate is configured to be placed over the threaded posts of the one or more fixation elements driven into the one or more locations of the second vertebra. The first and second plates comprise one or more apertures configured to receive the one or more fixation elements. The spine fixation assembly may further include one or more locking elements configured to attach each of the posts of the one or more fixation elements to the plates, thereby securing the plates to the one or more fixation elements. The first plate is also movable relative to the second plate along a longitudinal and/or a horizontal axis of the plates. These motions may be via a ratcheting mechanism. The plates may have triangular shape, rectangular shape, circular shape, semi-circular shape, oval shape, trapezoidal shape or elliptical shape. Each of the plates may comprise a central aperture configured to provide access and line of vision to the under laying first and second vertebras and to an intervertebral space between the first and second vertebras. The apertures are dimensioned to allow the posts to pass through and the flanges not to pass through, so that the plates sit on top of the flanges. The locking elements comprise threads dimensioned to engage threads in the posts. The first vertebra may be adjacent or not adjacent to the second vertebra. The first and second vertebras may be separated by at least a third vertebra and the plates are dimensioned to overlie the first, second and third vertebras. The spine fixation may further include a third plate configured to be attached to one or more locations of a third vertebra and the third plate is pivotally connected to the second plate. The third plate may be also movable relative to the second plate along a longitudinal or horizontal axis of the plates.

In general in another aspect the invention features a spine fixation method for connecting a first vertebra to a second vertebra including attaching a first plate to one or more locations of said first vertebra and then attaching a second plate to one or more locations of said second vertebra. The first plate is pivotally connected to said second plate.

Among the advantages of this invention may be one or more of the following. The improved spine fixation system allows motion between the segments to be fused away from the fixation points. The dynamic fixation system provides bidirectional motion between the fused segments during compression (neck flexion) and distraction (extension and lying supine). The plates are allowed to pivot and/or slide longitudinally and/or horizontally relative to each other at a point between the fused segments. The plates can be placed at an angle relative to each other. This new dynamic plating system offers superior fusion rates since it allows continuous graft loading and natural graft subsidence while acting as a block to anterior graft displacement.

BRIEF DESCRIPTION OF THE DRAWINGS

Referring to the figures, wherein like numerals represent like parts throughout the several views.

DETAILED DESCRIPTION OF THE INVENTION

Figure 1:
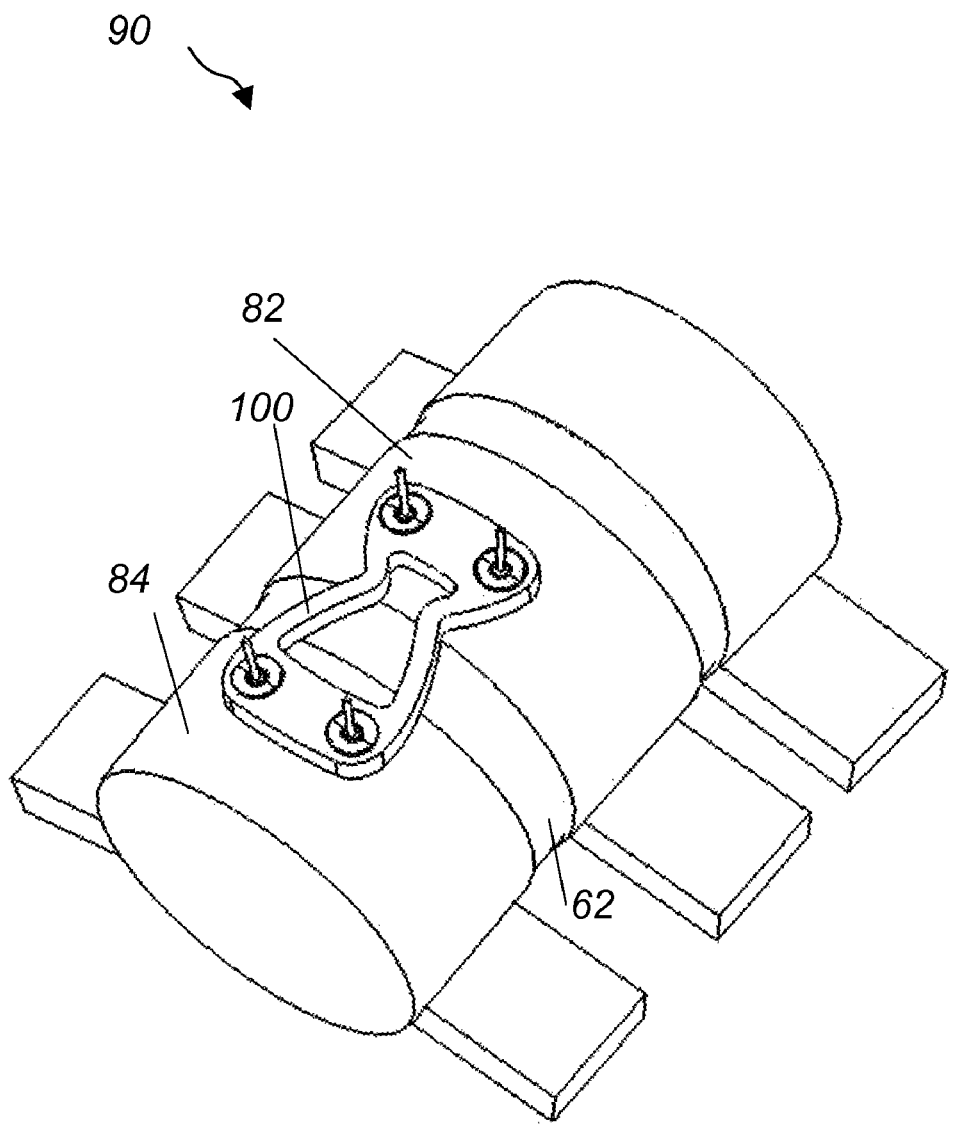
FIG. 1 is a front perspective view of a top loading, one-level, fixed cervical fusion plate connecting two adjacent vertebras.
Figure 2:
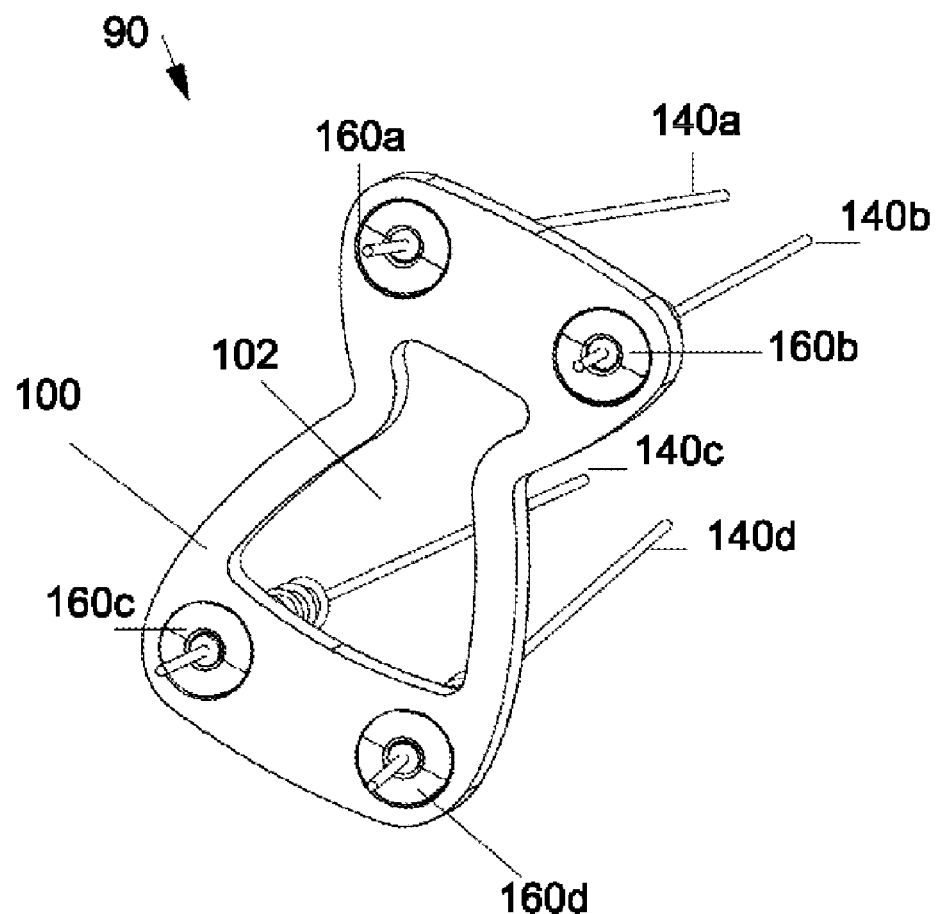
FIG. 2 is a front perspective view of the cervical fusion plate of FIG. 1.
Figure 3:
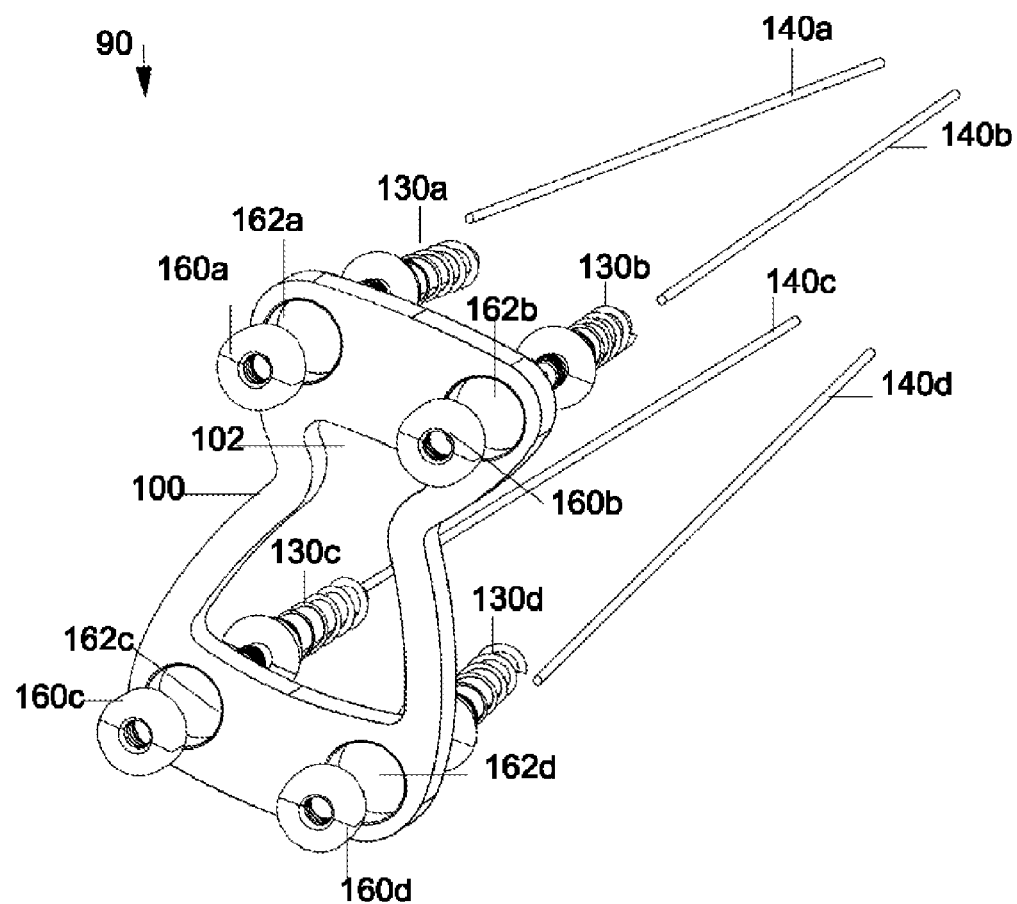
FIG. 3 is an exploded view of the cervical plate of FIG. 2.
Figure 4A:
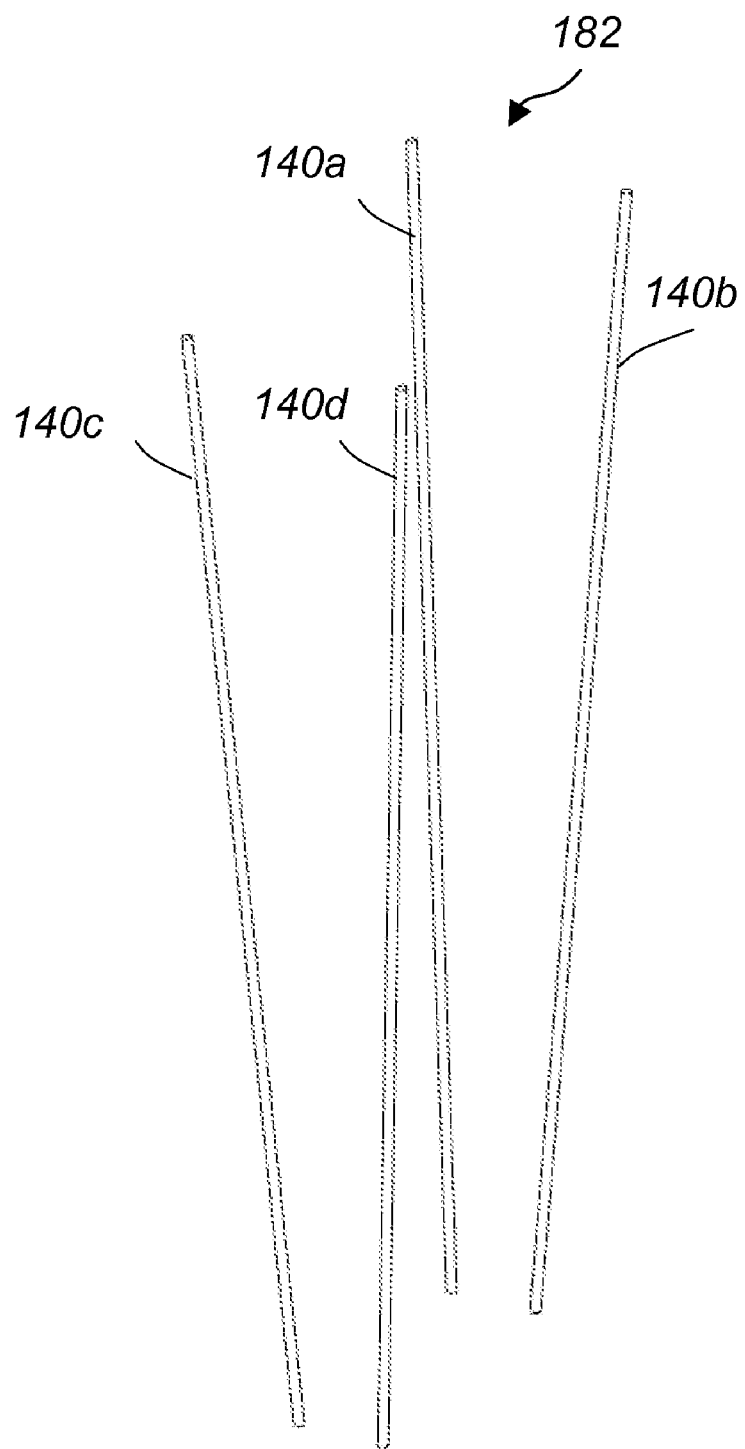
FIGS. 4A, 4B, 4C, 4D depict the steps for attaching the cervical plate of FIG. 1 to the vertebras.
Figure 4B:
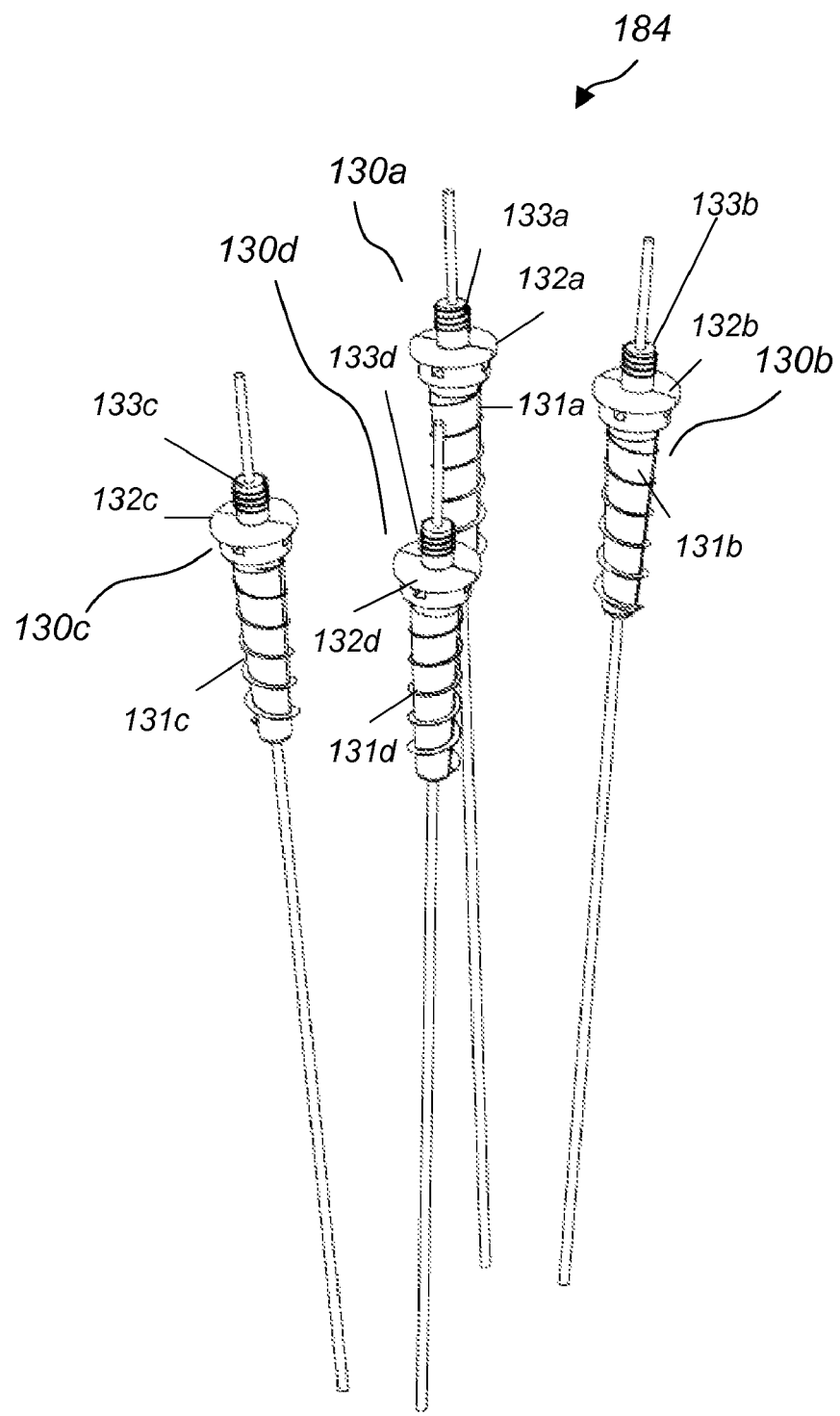
Figure 4C:
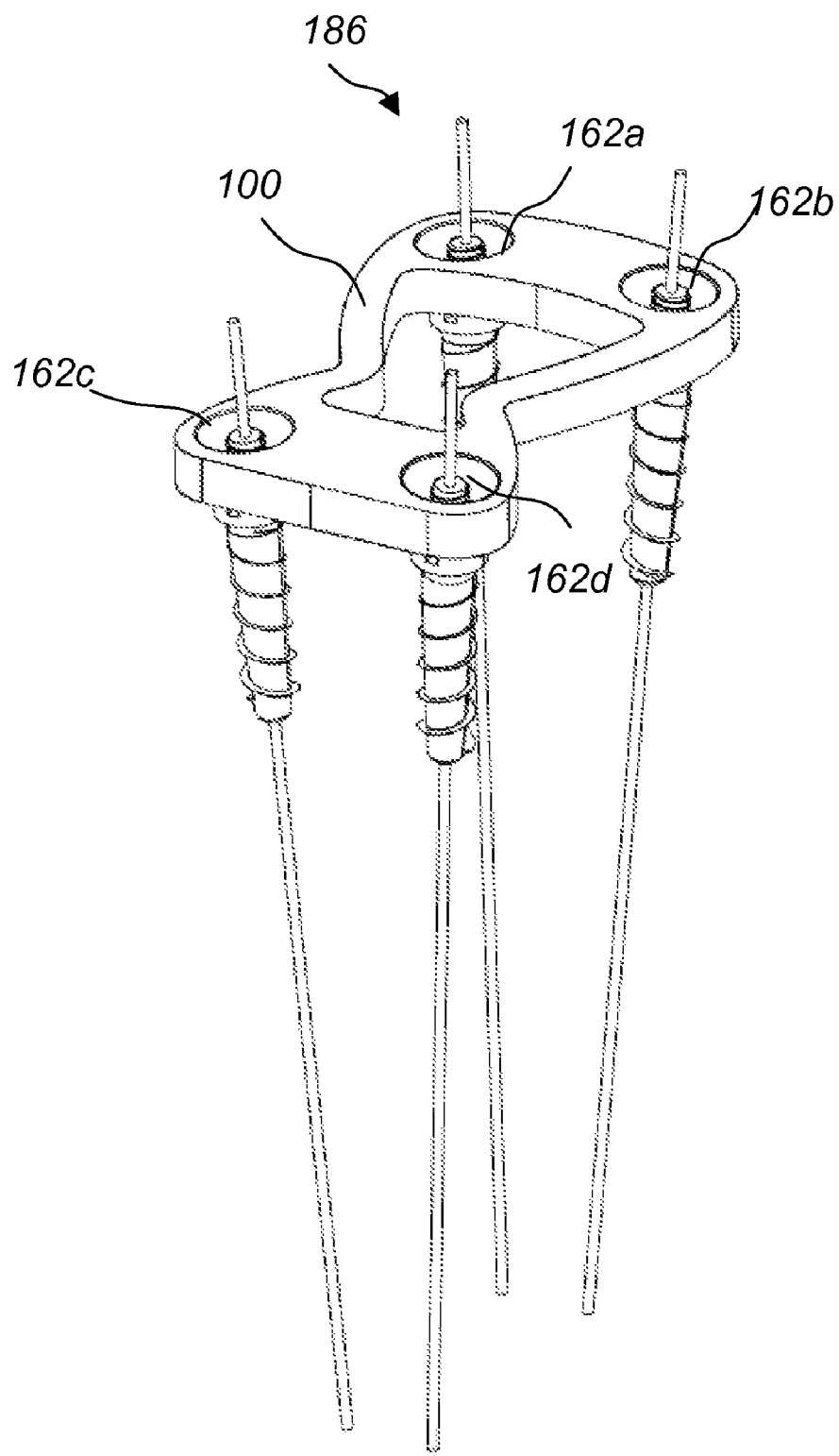
Figure 4D:
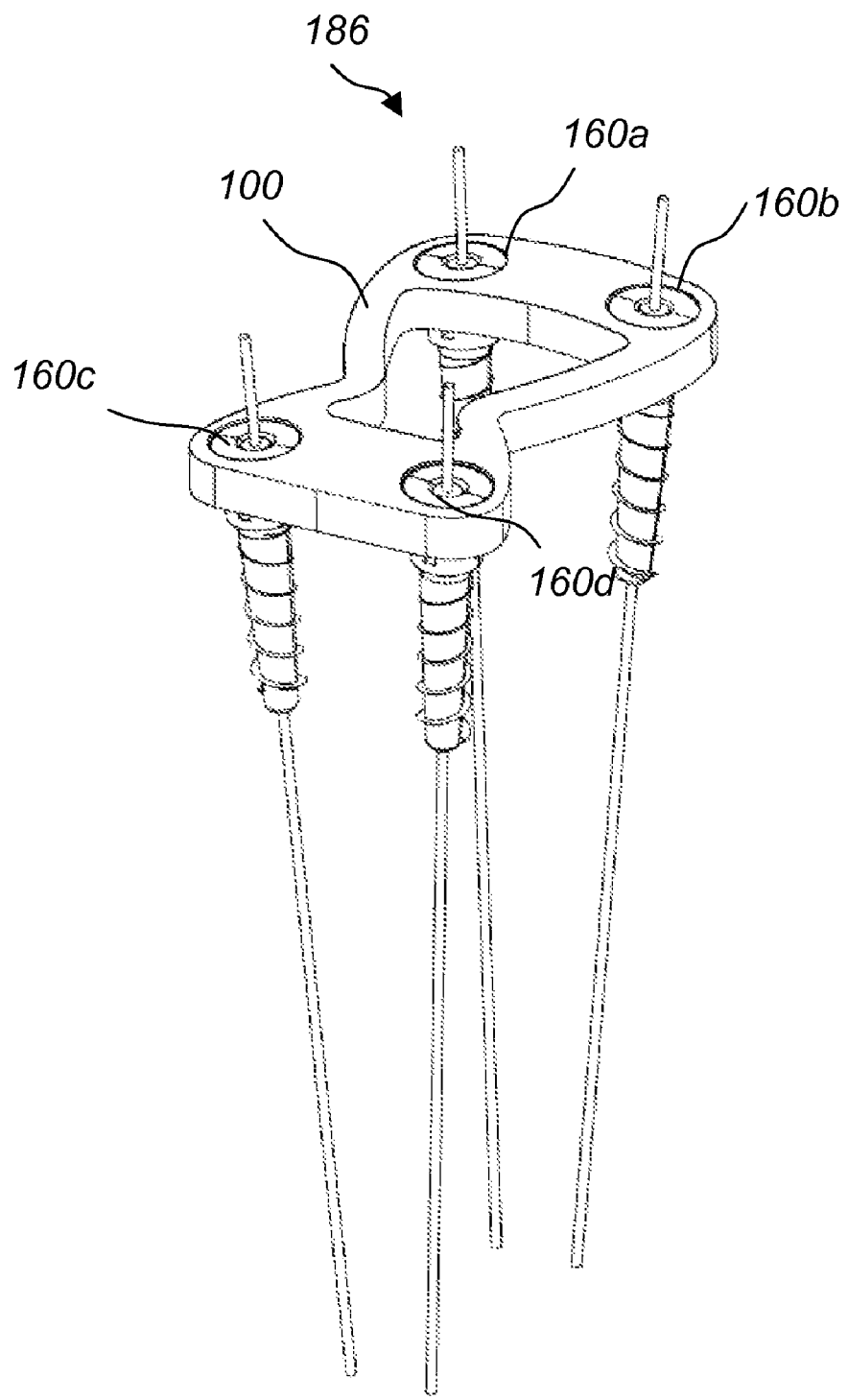

Referring to FIG. 1, FIG. 2 and FIG. 3, an anterior one-level fixed cervical fusion system 90 includes a top loading, one-level fixed cervical plate 100 that connects two adjacent vertebras 82 and 84. The fixed cervical plate 100 is attached to the vertebras 82 and 84 via four screws 130a, 130b and 130c, 130d, respectively. The fixed cervical plate 100 has an hourglass shape and an hourglass shaped aperture 102 centered in the middle of the plate 100. Aperture 102 provides visibility and access to the vertebras 82, 84 and disc 62 below the plate 100. Plate 100 also has four holes 162a, 162b, 162c and 162d located in the four corners of the plate. Holes 162a, 162b, 62c, 162d are dimensioned to receive the four screws 130a, 130b, 130c, 130d, respectively.

Referring to FIGS. 4A, 4B, 4C, 4D, the process for attaching the plate 100 to the adjacent vertebras 82, 84 includes the following steps. First, four k-wires 140a, 140b and 140c, 140d are inserted into the vertebras 82 and 84, respectively (182). Next, four screws 130a, 130b and 130c, 130d are driven into the vertebras 82 and 84, respectively, using the four k-wires 140a, 140b, and 140c, 140d, as guides respectively (184). Each screw has a threaded body 131, a flange 132 on top of the threaded body 131 and a threaded post 133 extending upwards from the flange 132. The threaded body 131 is driven into the vertebra while the flange 132 and the threaded post 133 remain above the vertebra. Next, the four holes 162a, 162b, 162c, 162d of the plate 100 are aligned with the four threaded posts 133a, 133b, 133c, 133d, respectively, and the plate 100 is top-loaded onto the screws 130a, 130b, 130c, 130d and lands onto the screw flanges 132a, 132b, 132c, 132d (186). The diameter of the screw flanges 132a-132d is larger than the diameter of holes 162a-162d, respectively, and the diameter of the screw posts 133a-133d is smaller than the diameter of holes 162a-162d, respectively. This geometric dimensioning allows the screw posts to pass through the plate holes while the plate stays on top of the flanges. Finally, four locking nuts 160a, 160b, 160c, 160d are screwed onto the threaded posts 133a, 133b, 133c, 133d, respectively, thereby securing the plate 100 onto the screws 130a, 130b, 130c, 130d (188).

Figure 5:
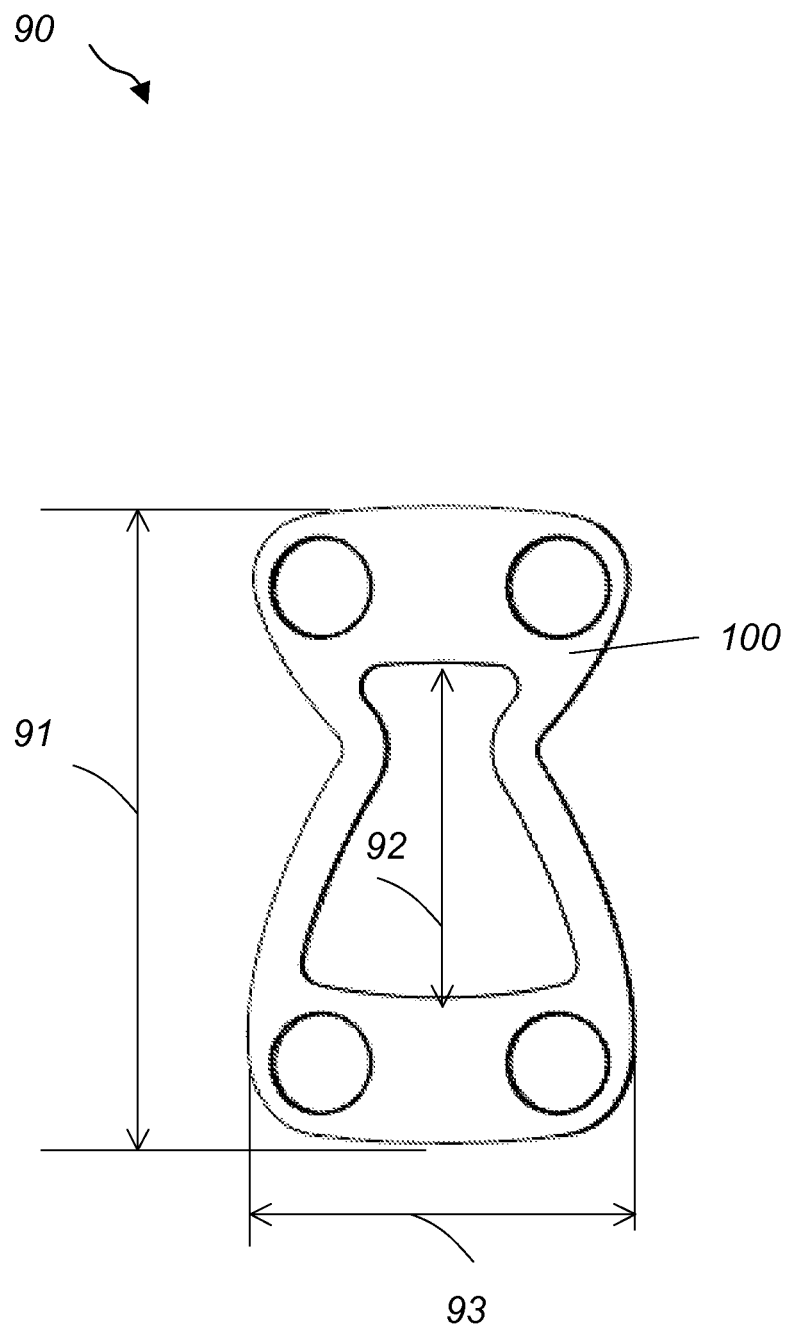
FIG. 5 is a front view of the cervical fusion plate of FIG. 1.

In one example, plate 100 has a height 91 of 30 mm, a width 93 of 17 mm and the aperture 102 has a height 92 of 15 mm, as shown in FIG. 5. The plate 100 may be made of metal such as stainless steel or titanium, plastic, bioabsorbable material and ceramic.

Figure 6:
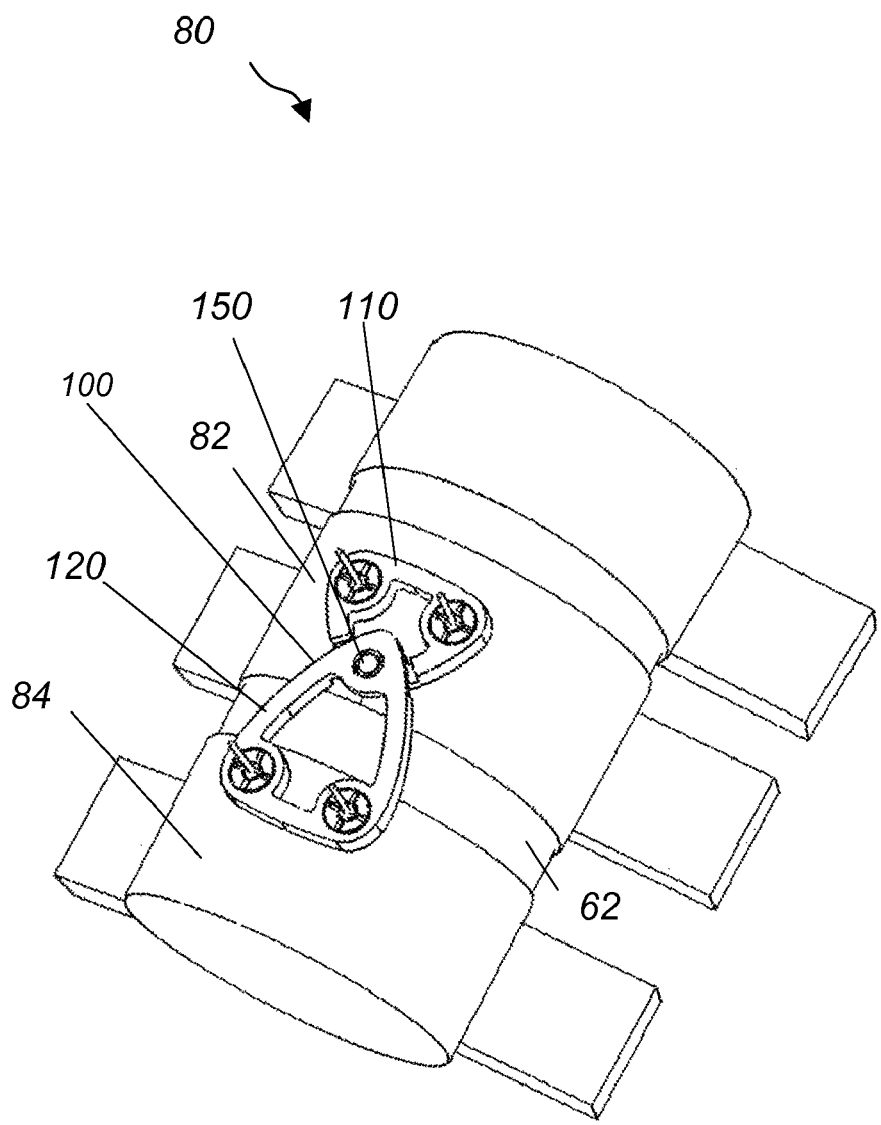
FIG. 6 is a front perspective view of a top loading, one-level, pivoting cervical fusion plate connecting two adjacent vertebras.
Figure 7:
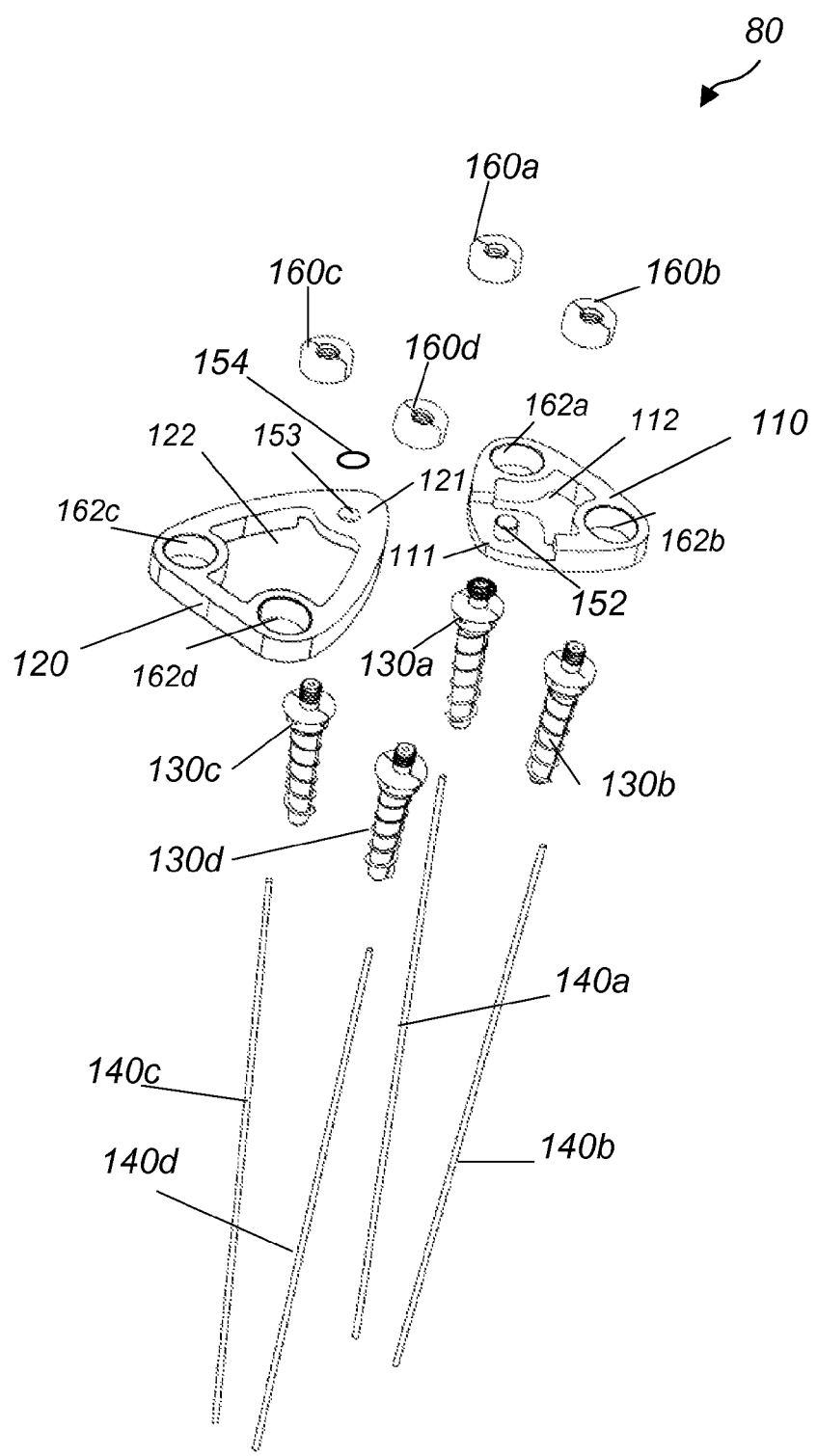
FIG. 7 is an exploded view of the cervical plate of FIG. 6.
Figure 8A:
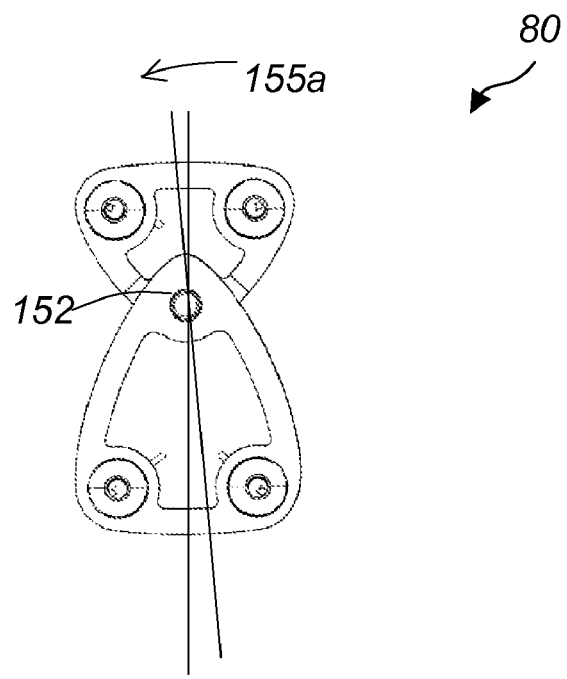
FIG. 8A depicts the counterclockwise pivoting motion of the top plate of FIG. 6.
Figure 8B:
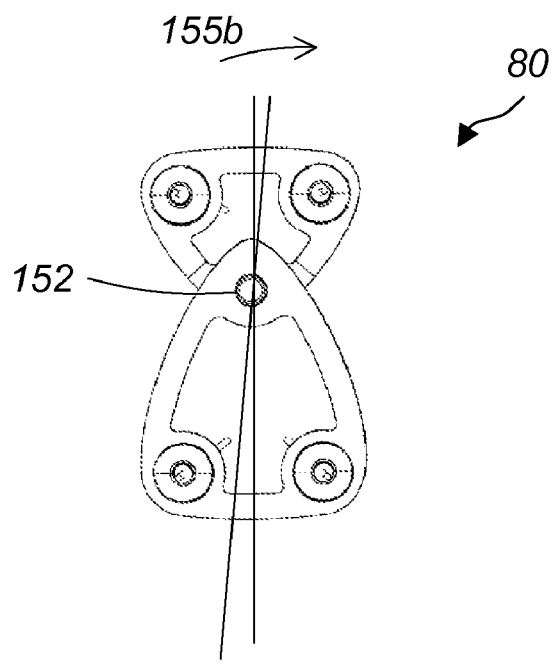
FIG. 8B depicts the clockwise pivoting motion of the top plate of FIG. 6.

Referring to FIG. 6 and FIG. 7, an anterior one-level pivoting cervical fusion system 80 includes a top loading, one-level pivoting cervical plate 100 that connects two adjacent vertebras 82 and 84. The pivoting cervical plate 100 is attached to the vertebras 82 and 84 via four screws 130a, 130b and 130c, 130d, respectively. The pivoting cervical plate 100, includes a triangular shaped top subplate 110 and a triangular shaped bottom subplate 120. The top subplate 110 is closest to the head of the patient and has an apex 111 facing down toward the bottom subplate 120. The bottom subplate 110 is closest to the patient's feet and has an apex 121 facing up toward the top subplate 110. The apex 111 of the top subplate 110 is pivotably connected to the apex 121 of the bottom subplate 120 at point 150, via a pivoting pin 152 that protrudes from the top surface of the apex 111 of the top subplate 110. The bottom subplate 120 has a hole 153 formed at the apex 121 for receiving the pivoting pin 152. A pivot cap 154 secures the top subplate 120 onto the pivot pin 152 while allowing the two subplates 110, 120 to pivot relative to each other counterclockwise 155a and clockwise 155b by a few degrees, as shown in FIG. 8A, and FIG. 8B, respectively. Each of the top and bottom subplates 110, 120, has two holes 162a, 162b and 162c, 162d, respectively, at the two corners opposite their respective apexes 111, 121. Holes 162a, 162b, 162c, 162d are dimensioned to receive the four screws 130a, 130b, 130c, 130d, respectively. The subplates 110, 120 are top loaded onto the posts of the four screws 130a, 130b, 130c, 130d, and are secured onto the flanges of the four screws 130a, 130b, 130c, 130d, with four locking nuts 160a, 160b, 160c, 160d, respectively, as described in FIG. 4D. The triangular subplates 110, 120 have central apertures 112, 122, that provide visibility and access to the vertebras 82, 84 and disc 62 below them.

Figure 9:
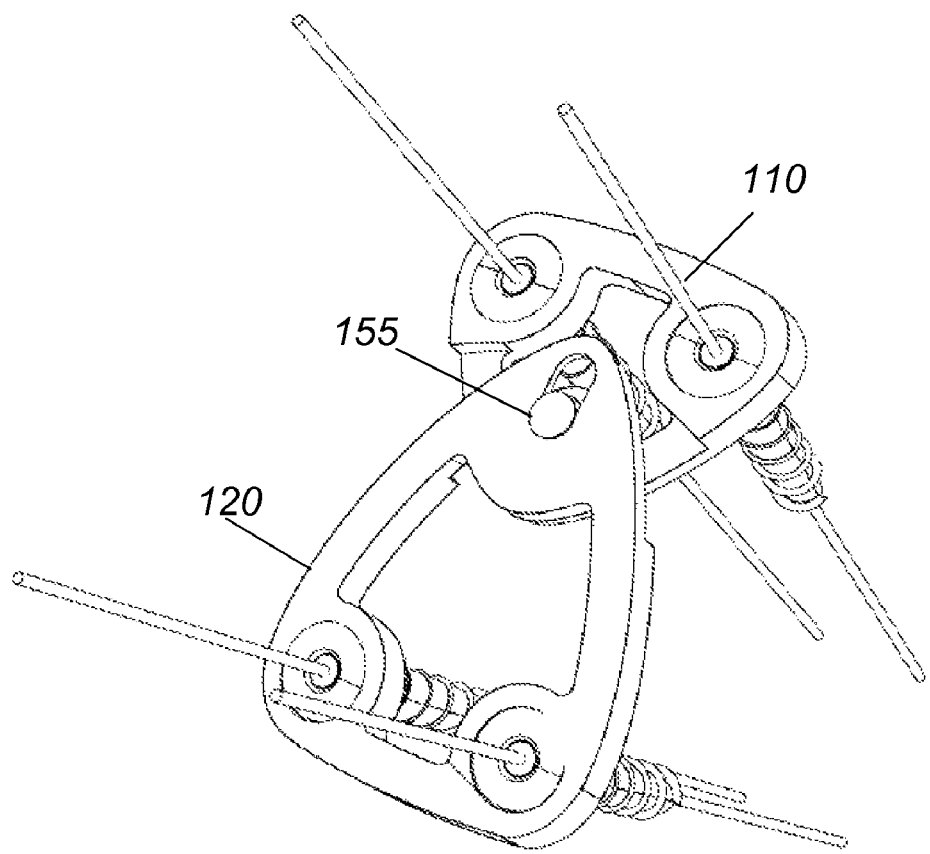
FIG. 9 is a front perspective view of a top loading, one-level, dynamic cervical fusion plate connecting two adjacent vertebras.
Figure 10:
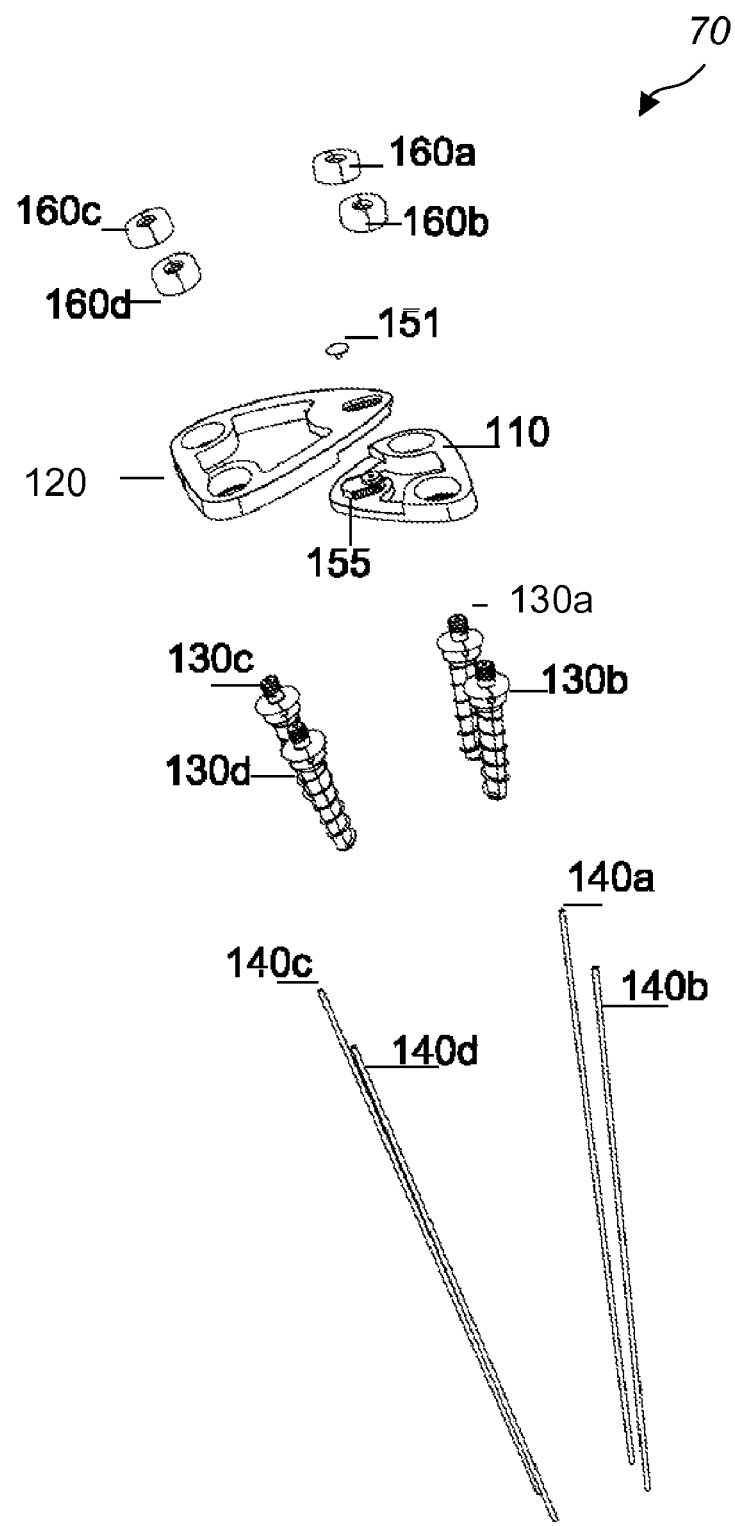
FIG. 10 is an exploded view of the cervical plate of FIG. 9.
Figure 11A:
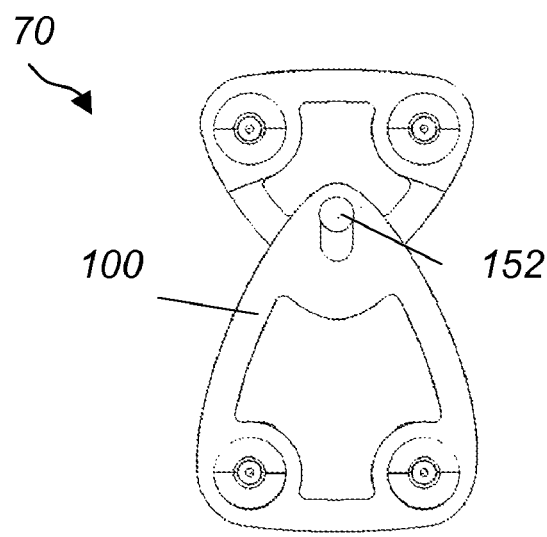
FIG. 11A depicts the upward motion of the top plate of FIG. 9.
Figure 11B:
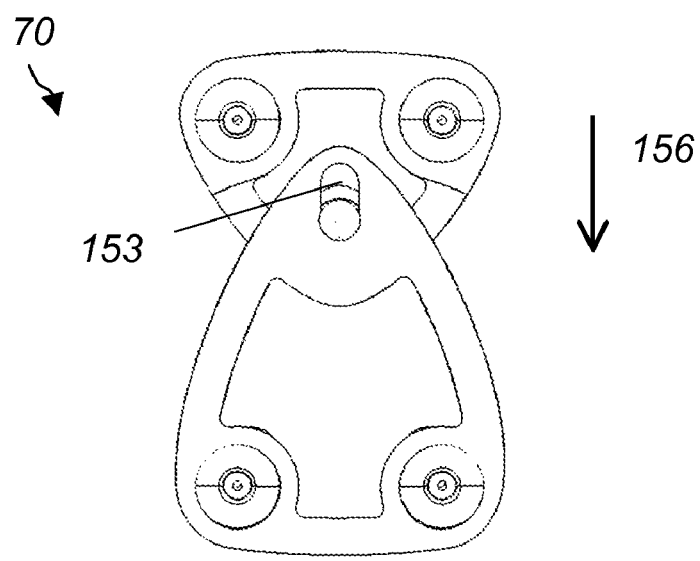
FIG. 11B depicts the downward motion of the top plate of FIG. 9.
Figure 12A:
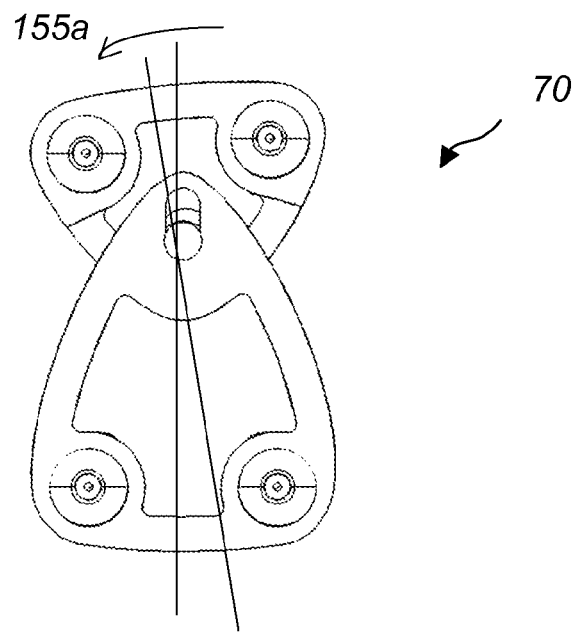
FIG. 12A depicts the counterclockwise motion of the top plate of FIG. 9.
Figure 12B:
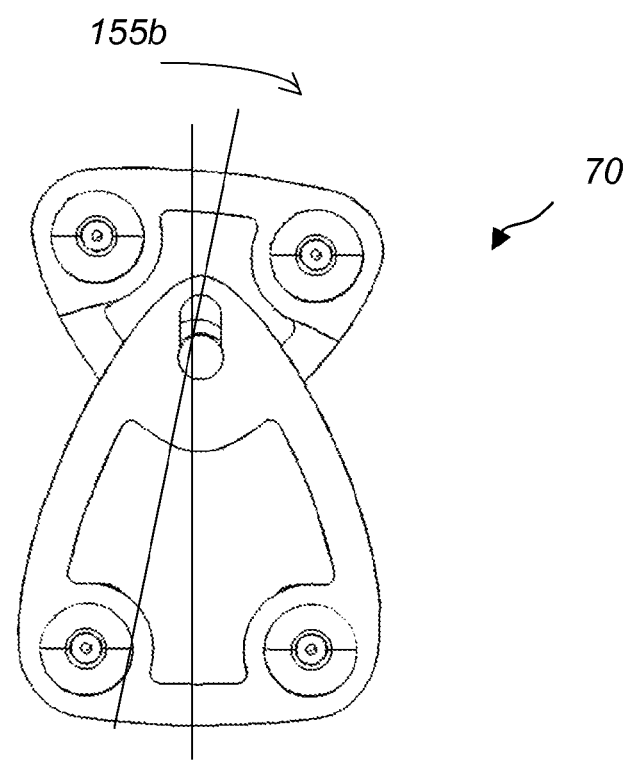
FIG. 12B depicts the clockwise motion of the top plate of FIG. 9.

Referring to FIG. 9, FIG. 10 and FIG. 11A, an anterior one-level dynamic stabilization system 70 includes a top loading, one-level dynamic plate 100 that connects two adjacent vertebras 82 and 84, shown in FIG. 6. The dynamic plate 100 is attached to the vertebras 82 and 84 via four screws 130a, 130b and 130c, 130d, respectively. The dynamic cervical plate 100, includes a triangular shaped top subplate 110 and a triangular shaped bottom subplate 120. The top subplate 110 slides down and pivots relative to the bottom subplate 120 via a ratchet and pivot mechanism 155, respectively. The top subplate 110 is closest to the head of the patient and has an apex 111 facing down toward the bottom subplate 120. The bottom subplate 110 is closest to the patient's feet and has an apex 121 facing up toward the top subplate 110. The apex 111 of the top subplate 110 is pivotably connected to the apex 121 of the bottom subplate 120 at point 155, via a pivoting pin 152 that protrudes from the top surface of the apex 111 of the top subplate 110, shown in FIG. 7. The bottom subplate 120 has an elongated hole 153 formed at the apex 121 for receiving the pivoting pin 152, shown in FIG. 11A and FIG. 11B. The elongated hole 153 includes a ratchet mechanism for providing the sliding motion of the top subplate 110 relative to the bottom subplate 120. The ratchet mechanism allows for one-way movement 156 of the top subplate 110 toward the bottom subplate 120, shown in FIG. 11A and FIG. 11B. In one example, the sliding movement has a span of 2 mm at 0.03 mm increments. In this embodiment, the bottom subplate 120 is not able to slide relative to the top subplate 110. A ratchet cap 151 secures the ratchet mechanism and the top subplate 120 onto the pivot pin 152 while allowing the two subplates 110, 120 to pivot relative to each other counterclockwise 155a and clockwise 155b by a few degrees, as shown in FIG. 12A, and FIG. 12B, respectively. Each of the top and bottom subplates 110, 120, has two holes 162a, 162b and 162c, 162d, respectively, at the two corners opposite their respective apexes 111, 121. Holes 162a, 162b, 62c, 162d are dimensioned to receive the four screws 130a, 130b, 130c, 130d, respectively. The subplates 110, 120 are top loaded onto the posts of the four screws 130a, 130b, 130c, 130d, and are secured onto the flanges of the four screws 130a, 130b, 130c, 130d, with four locking nuts 160a, 160b, 160c, 160d, respectively. The triangular subplates 110, 120 have central apertures 112, 122, that provide visibility and access to the vertebras 82, 84 and disc 62 below them.

Figure 13:
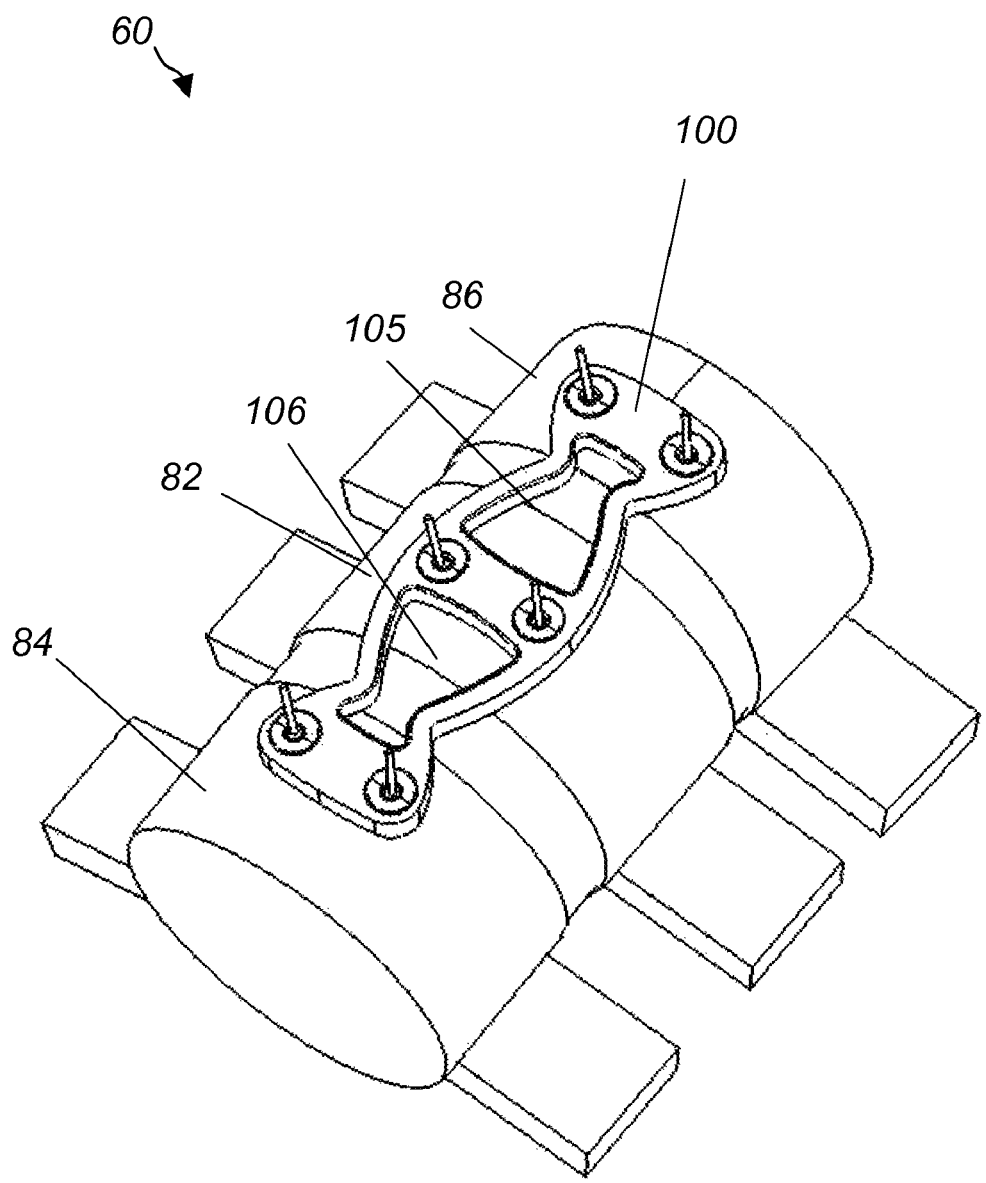
FIG. 13 is a front perspective view of a top loading, two-level, fixed cervical fusion plate connecting three adjacent vertebras.
Figure 14:
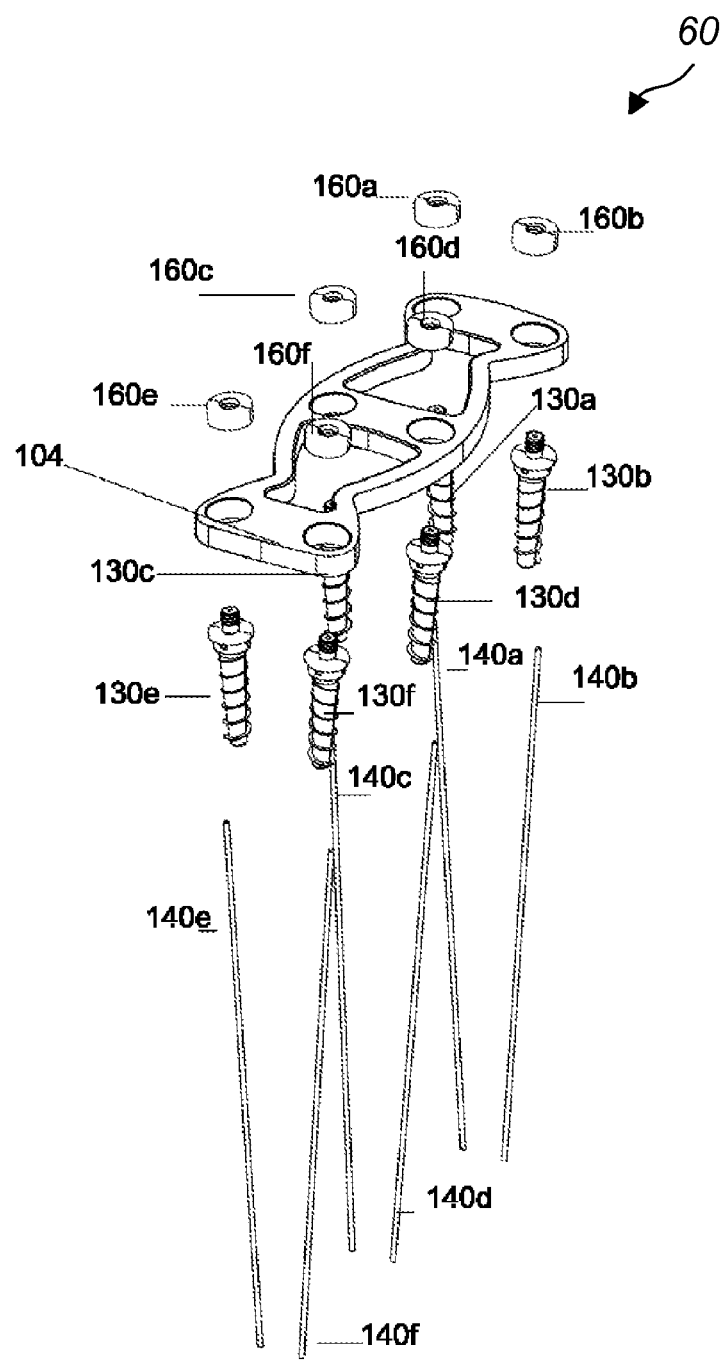
FIG. 14 is an exploded view of the cervical plate of FIG. 13.

Referring to FIG. 13 and FIG. 14, an anterior two-level fixed cervical fusion system 60 includes a top loading, two-level fixed cervical plate 100 that connects three adjacent vertebras 82, 84, and 86. The fixed cervical plate 100 is attached to the vertebras 82, 84 and 86 via six screws 130a, 130b, 130c, 130d, 130e, and 130f. The fixed cervical plate 100 has a shape of two adjacent hourglasses that are merged together. The plate 100 has two hourglass shaped apertures 105, 106 centered in the top and bottom of the plate 100. Apertures 105, 106 provide visibility and access to the vertebras 82, 84, 86 and disc 62 below the plate 100. Plate 100 also has six holes 162a, 162b, 162c, 162d, 162e and 162f located in the four corners and center of the plate. Holes 162a, 162b, 62c, 162d, 162e, 162f are dimensioned to receive the six screws 130a, 130b, 130c, 130d, 130e, 130f, respectively. Six locking nuts 160a, 160b, 160c, 160d, 160e, 160g are screwed onto the threaded posts of the screws, thereby securing the plate 100 onto the screws. The process of attaching the plate 100 to the adjacent vertebras 82, 84, 86 is as described above.

Figure 15:
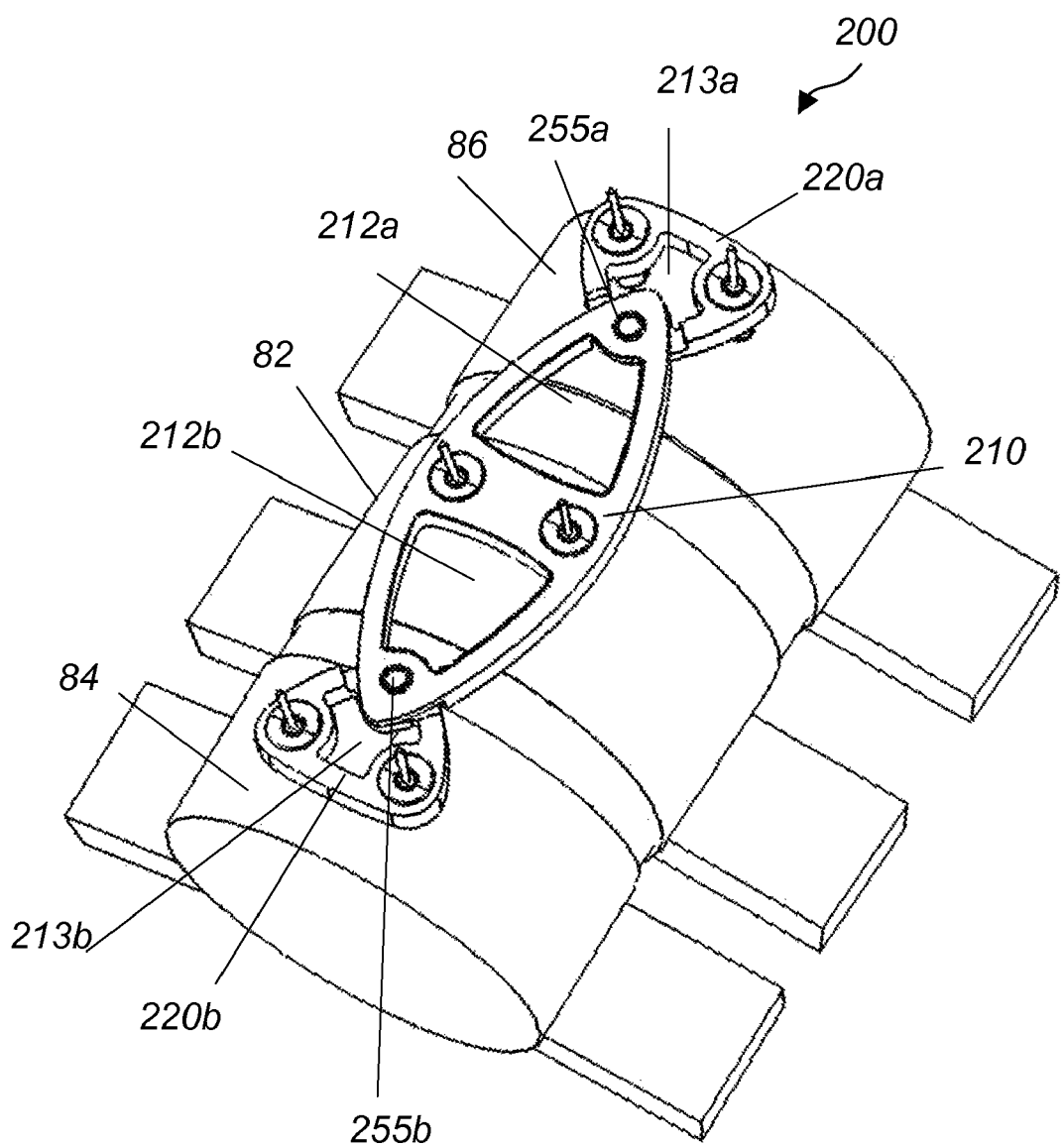
FIG. 15 is a front perspective view of a top loading, two-level, pivoting cervical fusion plate connecting three adjacent vertebras.
Figure 16:
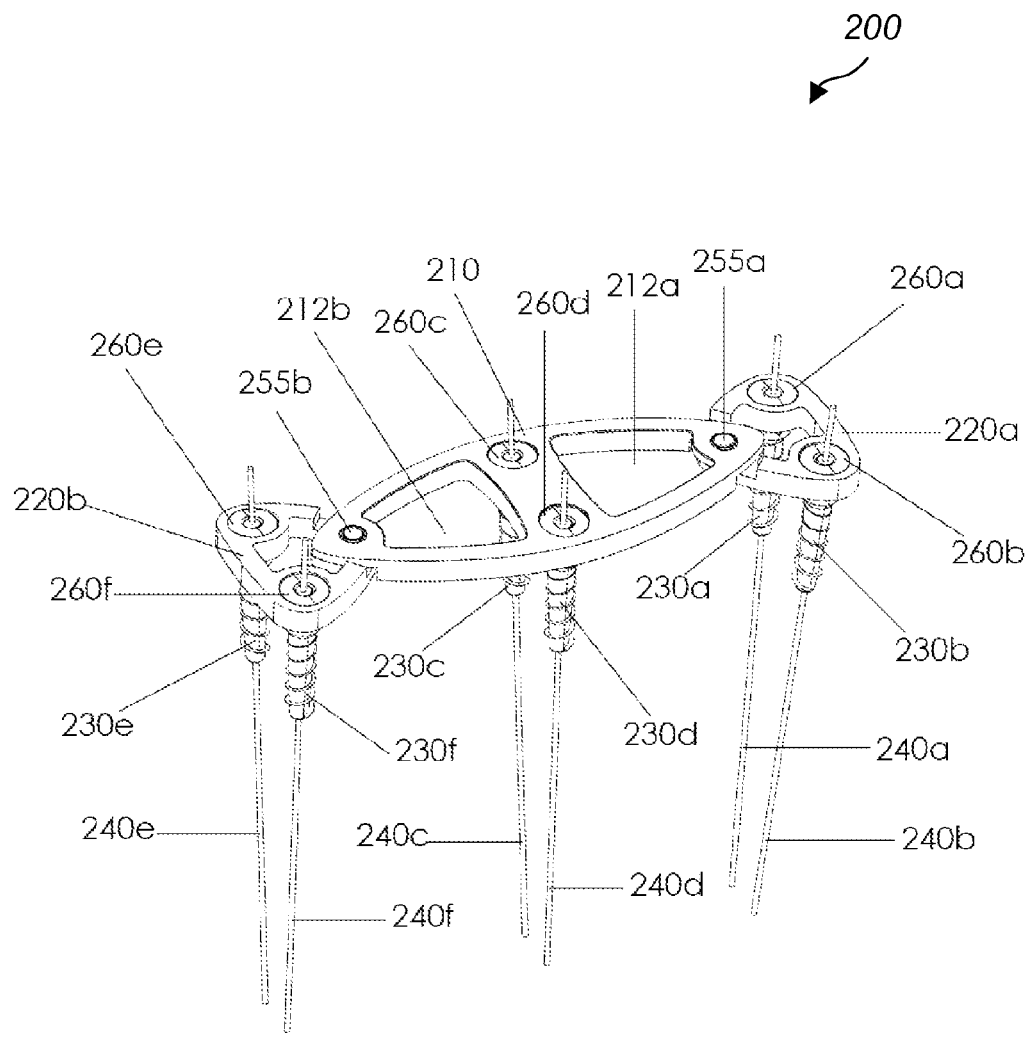
FIG. 16 is a perspective view of the cervical plate of FIG. 15.

Referring to FIG. 15 and FIG. 16, an anterior two-level pivoting cervical fusion system 200 includes a top loading, two-level pivoting cervical plate 100 that connects three adjacent vertebras 82, 84, and 86. The pivoting cervical plate 100 is attached to the vertebras 82, 84 and 86 via six screws 130a, 130b, 130c, 130d, 130e, and 130f. The pivoting cervical plate 100, includes a triangular shaped top plate 220a, a diamond shaped middle subplate 210 and a triangular shaped bottom plate 220b. The top subplate 220a pivots relative to the middle subplate 210 around pivot point 255a. The bottom subplate 220b pivots relative to the middle subplate 210 around pivot point 255b. The top subplate 220a is closest to the head of the patient and has an apex facing down towards the top apex of the middle subplate 210. The bottom subplate 220b is closest to the patient's feet and has an apex facing up toward the bottom apex of the middle subplate 210. The apex of the top subplate 220a is pivotably connected to the top apex of the middle subplate 210 at point 255a. The apex of the bottom subplate 220b is pivotably connected to the bottom apex of the middle subplate 210 at point 255b. The pivoting mechanism is similar to the mechanism in FIG. 6 and it allows the top and bottom subplates 220a, 220b to pivot relative to the middle subplate 210 counterclockwise and clockwise by a few degrees. Each of the top and bottom subplates 220a, 220b, has two holes 262a, 262b and 262e, 262f, respectively, at the two corners opposite their respective apexes, and the middle subplate 210 has two holes 262c, 262d in its middle corners. Holes 262a, 262b, 262c, 162d, 262e, 262f are dimensioned to receive six screws 230a, 230b, 230c, 230d, 230e, 230f, respectively. The subplates 220a, 220b, 210 are top loaded onto the posts of the screws and are secured onto the flanges of the screws with locking nuts 260a, 260b, 260c, 260d, 260e, 260f, respectively. The triangular subplates 220a, 220b have central apertures 213a, 213b and the middle subplate 210 has two central apertures 212a, 212b, that provide visibility and access to the vertebras 82, 84, 86 and discs below them. The process of attaching the plate 100 to the adjacent vertebras 82, 84, 86 is as described above.

Figure 17:
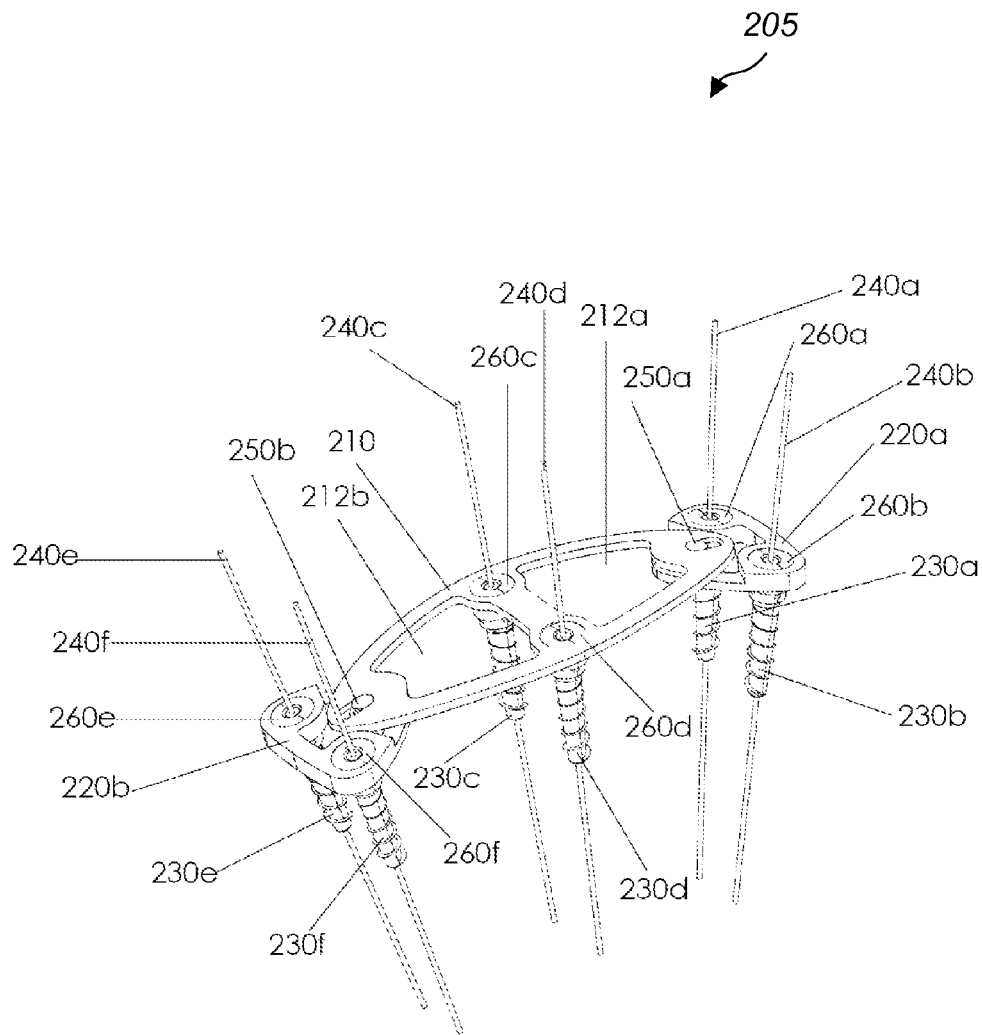
FIG. 17 is a perspective view of a top loading, two-level, dynamic cervical fusion plate connecting three adjacent vertebras.
Figure 18:
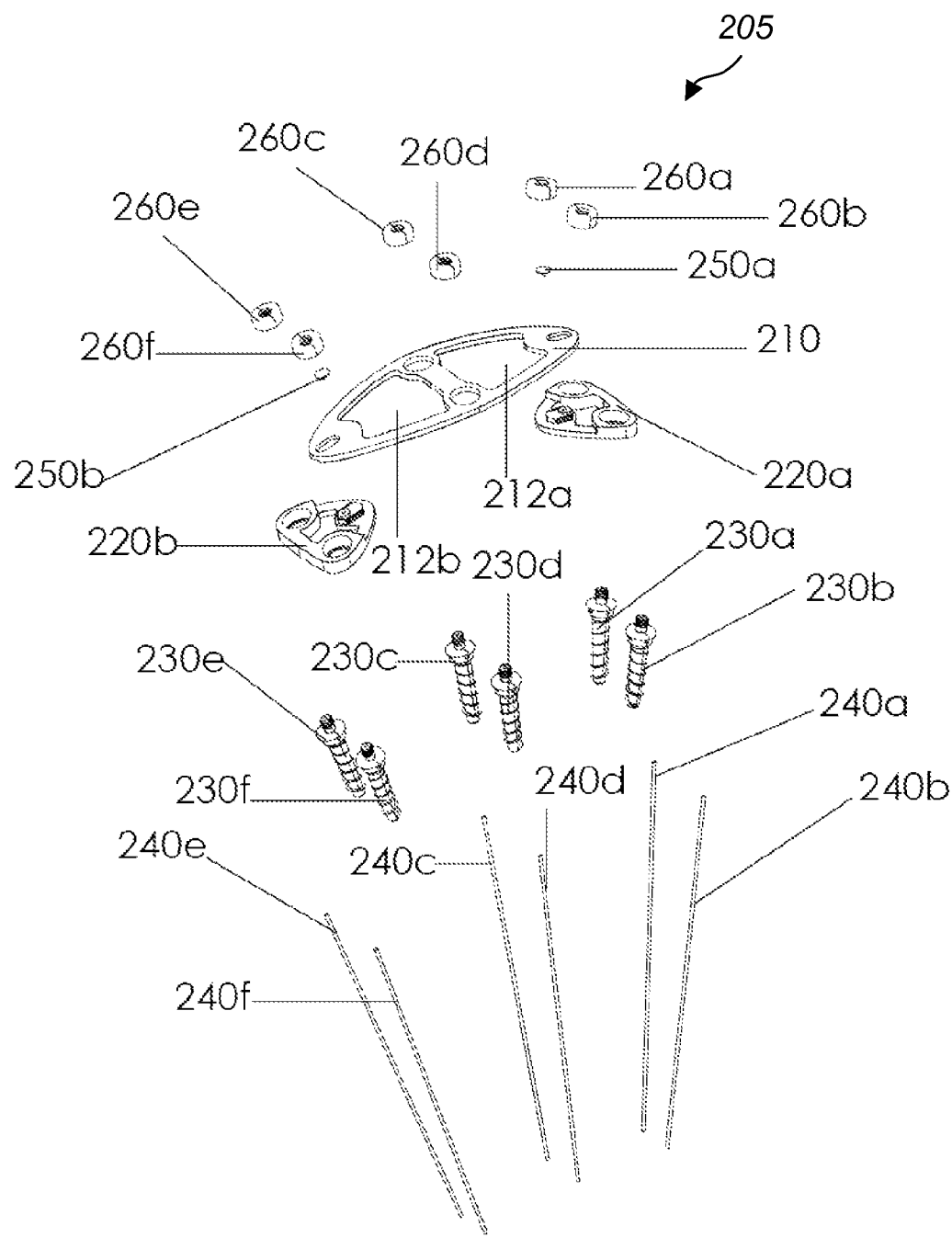
FIG. 18 is an exploded view of the cervical plate of FIG. 17.

Referring to FIG. 17 and FIG. 18, an anterior two-level dynamic stabilization system 205 includes a top loading, two-level dynamic cervical plate 100 that connects three adjacent vertebras 82, 84, and 86. The dynamic cervical plate 100 is attached to the vertebras 82, 84 and 86 via six screws 230a, 230b, 230c, 230d, 230e, and 230f The dynamic cervical plate 100, includes a triangular shaped top plate 220a, a diamond shaped middle subplate 210 and a triangular shaped bottom plate 220b. The top subplate 220a slides and pivots relative to the middle subplate 210 around pivot point 250a via a ratchet and pivot mechanism, as described above in FIG. 9. The bottom subplate 220b slides and pivots relative to the middle subplate 210 around pivot point 250b via a ratchet and pivot mechanism as described for the embodiment of FIG. 9. The top subplate 220a is closest to the head of the patient and has an apex facing down toward the top apex of the middle subplate 210. The bottom subplate 220b is closest to the patient's feet and has an apex facing up toward the bottom apex of the middle subplate 210. The apex of the top subplate 220a is slidably and pivotably connected to the top apex of the middle subplate 210 at point 255a. The apex of the bottom subplate 220b is slidably and pivotably connected to the bottom apex of the middle subplate 210 at point 255b. The ratchet and pivoting mechanism is similar to the mechanism in FIG. 9 and it allows the top and bottom subplates 220a, 220b to slide by about 2 mm and pivot relative to the middle subplate 210 counterclockwise and clockwise by a few degrees. Each of the top and bottom subplates 220a, 220b, has two holes 262a, 262b and 262e, 162f, respectively, at the two corners opposite their respective apexes, and the middle subplate 210 has two holes 262c, 262d in its middle corners. Holes 262a, 262b, 262c, 162d, 262e, 262f are dimensioned to receive six screws 230a, 230b, 230c, 230d, 230e, 230f, respectively. The subplates 220a, 220b, 210 are top loaded onto the posts of the screws and are secured onto the flanges of the screws with locking nuts 260a, 260b, 260c, 260d, 260e, 260f, respectively. The triangular subplates 220a, 220b have central apertures 213a, 213b and the middle subplate 210 has two central apertures 212a, 212b, that provide visibility and access to the vertebras 82, 84, 86 and discs below them.

Figure 19A:
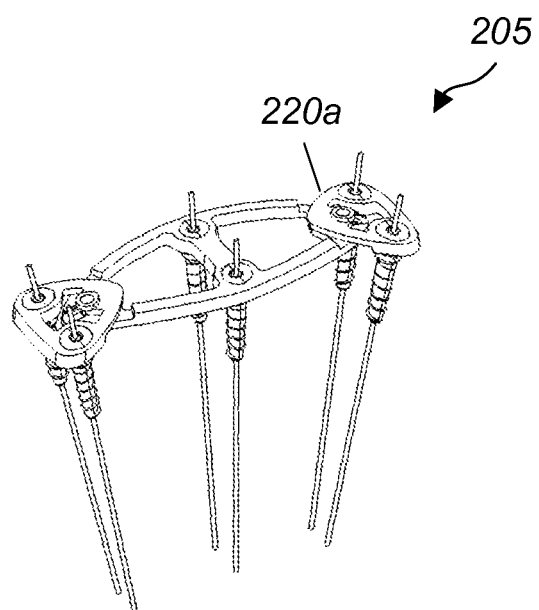
FIGS. 19A, 19B, 19C depict the steps of modifying the two-level, dynamic cervical fusion plate of FIG. 17 to dynamically attach it to a fourth vertebra.
Figure 19B:
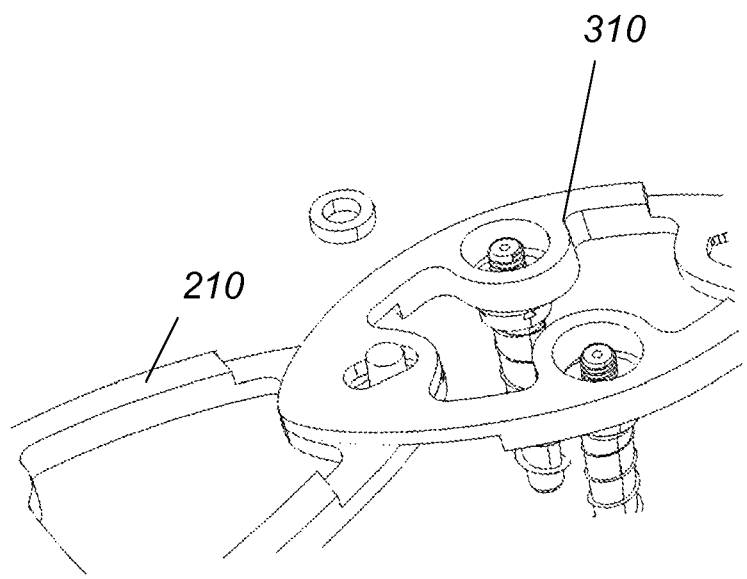
Figure 19C:
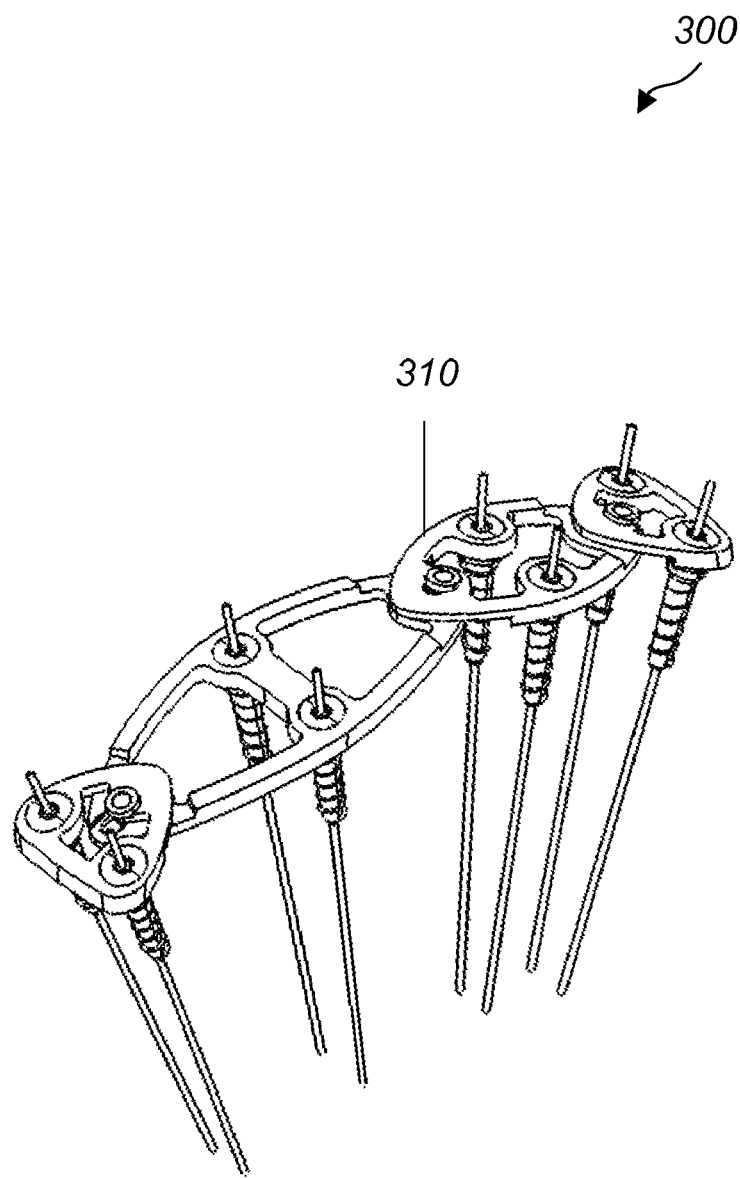

In the embodiment of FIGS. 19A, 19B and 19C, an anterior two-level dynamic stabilization system 205 is already in place and the patient needs to have the next level of vertebra stabilized. In this case, the top subplate 220a, is removed and is replaced with a diamond shaped sub-plate 310, shown in FIG. 19B. Next, the top subplate is re-installed on the top of the diamond subplate 310, as shown in FIG. 19C. The attachment of the diamond shaped subplate 310 to the middle subplate 210 is not dynamic, i.e., it allows pivoting but not sliding, whereas the connection of the top subplate 220a to the diamond shaped subplate 310 is dynamic.

Figure 20:
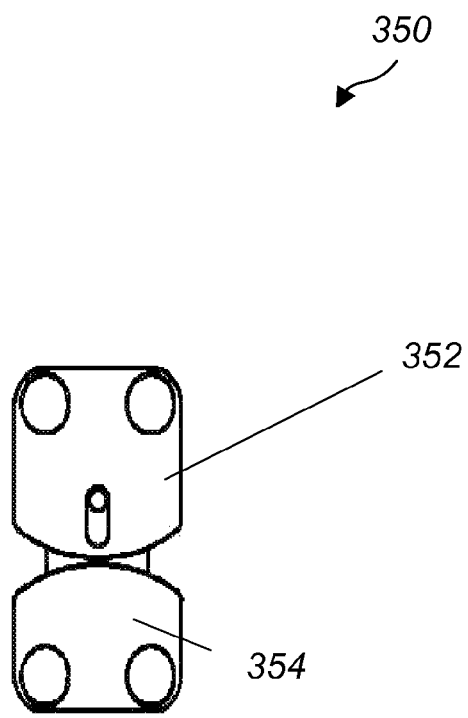
FIG. 20 is another embodiment of a top loading, one-level, dynamic cervical fusion plate connecting two adjacent vertebras.
Figure 21:
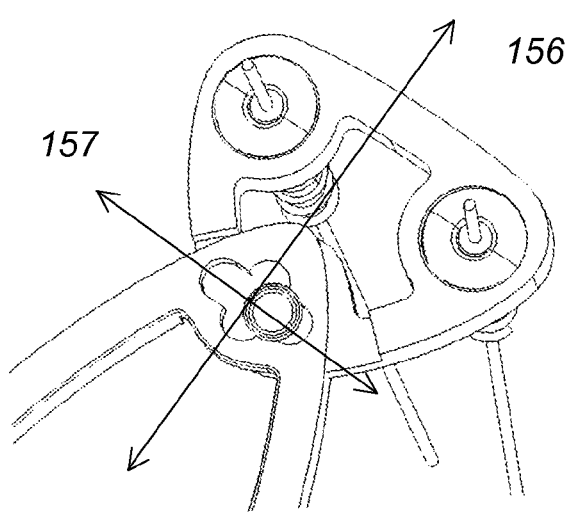
FIG. 21 is another embodiment of a top loading, one-level, dynamic cervical fusion plate.

Other embodiments are within the scope of the following claims. For example, the bottom subplate may be able to slide relative to the top subplate in the dynamic stabilization system of FIG. 9. The motion of the top subplate 110 relative to the bottom subplate 120 may be vertical 156, horizontal 157, pivoting 155 and any combinations thereof, as shown in FIG. 21 and FIG. 8A-8B. The plate 100 may be placed onto the cervical bone first and then may be attached to the bone by screwing the screws 130a, 130b, 130c, 130d through the holes 162a, 162b, 162c, 162d, into the bone and then securing the screws onto the plate 100 with the locking nuts 160a, 160b, 160c, 160d, respectively. The screws 130a, 130b, 130c, 130d may be multi-axial screws with locking housings and "starfish" shape locking nuts that locks into the screw housings. Alternatively, the screws may have a spherically shaped head on the screw with textured surface that allows for angular mounting with a concaved spherically shaped hole or chamfered shaped hole with textured surface in the plate. Then a threaded bolt would be screwed onto the top of the spherically shaped head and lock the system together. Alternatively, multi-axial and oversized holes are formed in the plate and "starfish" shaped locking nuts lock the screws onto the plate. The subplates may have other shapes including rectangular (shown in FIG. 20), square, circular, oval or polygonal.

Several embodiments of the present invention have been described. Nevertheless, it will be understood that various modifications may be made without departing from the spirit and scope of the invention. Accordingly, other embodiments are within the scope of the following claims.

What is claimed is:

1. A spine fixation assembly for connecting a first vertebra to a second vertebra comprising:
    first and second guide wires configured to be removably inserted into first and second locations of said first vertebra and third and fourth guide wires configured to be removably inserted into first and second locations of said second vertebra;
    first and second fixation elements configured to be driven into said first and second locations of said first vertebra and third and fourth fixation elements configured to be driven into said first and second locations of said second vertebra, respectively, wherein each of said fixation elements comprises a threaded body, a flange extending from an end of said threaded body, a threaded post extending from said flange and a through bore extending longitudinally through said threaded body said flange and said post, and wherein said corresponding guide wire is dimensioned to pass through said through bore;
    a first plate configured to be top-loaded over said threaded posts of said first and second fixation elements driven into said first and second locations of said first vertebra;
    a second plate configured to be top-loaded over said threaded posts of said third and fourth fixation elements driven into said first and second locations of said second vertebra;
    wherein said first and second plates comprise one or more apertures configured to receive said one or more fixation elements and wherein the diameters of said apertures are smaller than the diameters of said fixation elements flanges; and
    wherein said first plate comprises an apex facing toward the second plate and wherein said second plate comprises an apex facing toward the first plate and wherein said first plate apex overlaps with said second plate apex and wherein said first plate is pivotally connected to said second plate via a pivot pin and wherein said pivot pin extends from said first plate and said second plate comprises an opening dimensioned to receive said pivot pin and wherein said pivot pin is perpendicular to said overlapping apexes of said first and second plates and wherein said first and second plates pivot relative to each other around a pivot axis being perpendicular to said first and second plates; and
    wherein said opening of the second plate comprises an elongated slot extending along a longitudinal axis wherein said longitudinal axis is perpendicular to said pivot axis and wherein said first plate is also movable relative to said second plate along said longitudinal axis.

2. The spine fixation assembly of claim 1 wherein said assembly further comprises a pivot cap configured to secure said second plate onto said pivot pin while allowing pivoting motion of said first and second plates relative to each other.

3. The spine fixation assembly of claim 2 further comprising one or more locking elements configured to attach each of said posts of said one or more fixation elements to said plates, thereby securing said plates to said one or more fixation elements.

4. The spine fixation assembly of claim 1 wherein said first plate is also movable relative to said second plate along a longitudinal axis via a ratcheting mechanism, wherein said longitudinal axis is perpendicular to said pivot axis.

5. The spine fixation assembly of claim 1 wherein said first plate is also movable relative to said second plate along a horizontal axis, wherein said horizontal axis is perpendicular to said pivot axis.

6. The spine fixation assembly of claim 1 wherein said each of said plates comprises a central aperture configured to provide access and line of vision to said under laying first and second vertebras and to an intervertebral space between said first and second vertebras.

7. The spine fixation assembly of claim 2 wherein said apertures are dimensioned to allow said posts to pass through and said flanges not to pass through, so that said plates sits on top of said flanges.

8. The spine fixation assembly of claim 3, wherein said locking elements comprise threads dimensioned to engage threads in said posts.

9. The spine fixation assembly of claim 1, wherein said first vertebra is adjacent to said second vertebra.

10. The spine fixation assembly of claim 1 wherein said first and second vertebras are separated by at least a third vertebra and wherein said plates are dimensioned to overlie said first, second and third vertebras.

11. The spine fixation assembly of claim 1 further comprising a third plate configured to be attached to first and second locations of a third vertebra and wherein said third plate is pivotally connected to said second plate and wherein said third and second plates pivot relative to each other around an axis perpendicular to said third and second plates.

12. The spine fixation assembly of claim 11 wherein said third plate is also movable relative to said second plate along a longitudinal axis of said plates.

13. The spine fixation assembly of claim 12 wherein said third plate is also movable relative to said second plate along a horizontal axis of said plates.

* * * * *